United States Patent
Tasaka et al.

(10) Patent No.: US 6,984,653 B2
(45) Date of Patent: Jan. 10, 2006

(54) HETEROCYCLIC COMPOUNDS, OXAZOLE DERIVATIVES, PROCESS FOR PREPARATION OF THE SAME AND USE THEREOF

(75) Inventors: Akihiro Tasaka, Suita (JP); Kenichiro Naito, Mino (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/491,377

(22) PCT Filed: Oct. 3, 2002

(86) PCT No.: PCT/JP02/10326

§ 371 (c)(1),
(2), (4) Date: Mar. 31, 2004

(87) PCT Pub. No.: WO03/031442

PCT Pub. Date: Apr. 17, 2003

(65) Prior Publication Data

US 2004/0242659 A1 Dec. 2, 2004

(30) Foreign Application Priority Data

Oct. 5, 2001 (JP) .................... 2001-309555

(51) Int. Cl.
A61K 31/4178 (2006.01)
C07D 263/32 (2006.01)
C07D 413/12 (2006.01)

(52) U.S. Cl. .................. 514/374; 548/235; 548/236
(58) Field of Classification Search ........... 548/236, 548/235; 514/374
See application file for complete search history.

(56) References Cited

U.S. PATENT DOCUMENTS

| | | | | |
|---|---|---|---|---|
| 5,656,655 | A * | 8/1997 | Spada et al. .......... | 514/415 |
| 6,211,215 | B1 | 4/2001 | Momose et al. | |
| 6,716,863 | B2 * | 4/2004 | Tasaka et al. ......... | 514/374 |
| 6,743,924 | B2 * | 6/2004 | Ikemoto et al. ....... | 548/255 |
| 2002/0173526 | A1 | 11/2002 | Tasaka et al. | |
| 2003/0069419 | A1 | 4/2003 | Ikemoto et al. | |
| 2004/0024035 | A1 * | 2/2004 | Tasaka et al. ......... | 514/374 |
| 2004/0053972 | A1 * | 3/2004 | Nara .................... | 514/341 |
| 2004/0058956 | A1 * | 3/2004 | Akiyama et al. ...... | 514/318 |
| 2004/0116330 | A1 * | 6/2004 | Naito et al. ........... | 514/2 |
| 2004/0138160 | A1 * | 7/2004 | Naito et al. ........... | 514/44 |

FOREIGN PATENT DOCUMENTS

| | | |
|---|---|---|
| EP | 1350792 | 10/2003 |
| EP | 1350793 | 10/2003 |
| WO | WO 9803505 A2 * | 1/1998 |
| WO | WO 200248141 A1 * | 6/2002 |
| WO | WO 2003059907 A1 * | 7/2003 |

OTHER PUBLICATIONS

Ross, J., et al., "Targeted Therapy in Breast Cancer: the HER–2/neu Gene and Protein," Molecular & Cellular Proteomics, vol. 3(4), pp. 379–398 (Apr. 2004), at p. 381, col. 2, lines 12–38.*

Ducreux, M., et al., "Emerging drugs in pancreatic cancer," Expert Opin. Emerg. Drugs, vol. 9(1), pp. 73–89 (May 2004), at p. 79, col. 1, line 19 et seq.*

Barton, J., et al., "Growth factors and their receptors: new targets for prostrate cancer therapy," Urology, vol. 58, Suppl. 2A, pp. 114–112 (Aug. 2001), at p. 118, col. 2, line 6, et seq.*

(Continued)

*Primary Examiner*—Joseph K. McKane
*Assistant Examiner*—Anthony J. Paviglianiti
(74) *Attorney, Agent, or Firm*—Mark Chao; Elaine M. Ramesh

(57) ABSTRACT

This invention provides a heterocyclic compound having potent tyrosine kinase-inhibiting activity represented by the formula:

(I)

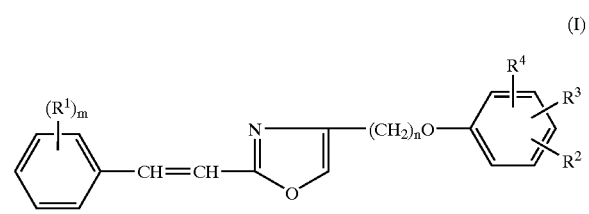

wherein m is an integer of 1 to 3; n is an integer of 1 or 2; $R^1$ is a halogen atom or an optionally halogenated $C_{1-2}$ alkyl group; each of $R^2$ and $R^3$ is, same or different, a hydrogen atom, a halogen atom, a lower alkyl group or a lower alkoxy group; $R^4$ is a group represented by the formula:

(IIa)

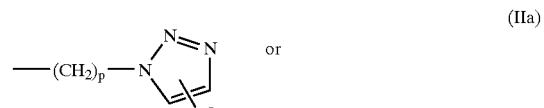

(IIb)

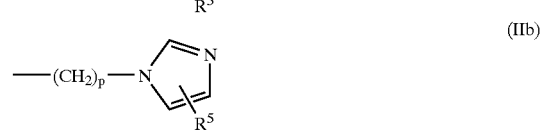

wherein p is an integer of 2 to 5; $R^5$ is a $C_{1-4}$ alkyl group substituted by alkoxycarbonyl group, carbamoyl group, carbamoyloxy group, alkylsulfonyl group, alkylsulfinyl group, sulfamoyl group, carbamoylamino group, alkylsulfonylamino group, acylamino group, and the like; or a salt thereof and a pharmaceutical composition comprising thereof.

10 Claims, No Drawings

OTHER PUBLICATIONS

Sawyers, C., "Rational therapeutic intervention in cancer: kinases as drug targets," Current Opinion in Genetics & Development, vol. 12(1), pp. 111–115 (Feb. 2002), at p. 111, lines 29–48; p. 113, lines 38–40; and p. 111, line 47 to p. 112, line 4.*

U.S. Food and Drug Administration, "FDA Statement on Iressa," released Dec. 17, 2004, p. 1, lines 8–9.*

"Avastin–Tarceva Combo Provides 'One–Two' Punch Against Lung Cancer," Science Daily (Jun. 7, 2004).*

Goldman, B., "For Investigational Targeted Drugs, Combination Trials pose Challenges," J. National Cancer Institute, vol. 95(23), pp. 1744–1746 (Dec. 3, 2003) at p. 1744, 1st col., lines 40–53.*

Robinson, D., et al., "The protein tyrosine kinase family of the human enome," Oncogene, vol. 19(49), pp. 5548–5557 (Nov. 2000), at Abstract; at p. 5548, col. 2, lines 42–50; at p. 5549, Table 1; and at p. 5550, Table 2b.*

Awada, A., et al., "The pipeline of new anticancer agents for breast cancer treatment in 2003," Critical Reviews in Oncology/Hematology, vol. 48(1), pp. 45–63 (Oct. 2003), at p. 46, col. 2, line 3.*

Nahta, R., et al., "Novel pharmacological approaches in the treatment of breast cancer," Expert Opin. Investigational Drugs, vol. 12(6), pp. 909–921 (Jun. 2003), at p. 913, col. 1, line 51 to p. 914, col. 2, line 14 ("Tyrosine kinase inhibitors").*

Nahta, R., et al., "Growth Factor Receptors in Breast Cancer: Potential for Therapeutic Intervention," The Oncologist, vol. 8(1), pp. 5–17 (Feb. 2003), at p. 8, ;line 19 et seq.*

Bartlett, J., et al., "The clinical evaluation of HER–2 status: which test to use?" J. Pathology, vol. 199(4), pp. 411–417 (Apr. 2003), at p. 412, col. 1, lines 4–18; also p. 412, lines 24–26; also at p. 411, col. 1, line 1 and col. 2, lines 1–5.*

J.S. Ross, et al., "The HER–2/neu Gene and Protein in Breast Cancer 2003: Biomaker and Target of Therapy", The Oncologist, (Aug. 2003), pp. 307–325, vol. 8.

* cited by examiner

HETEROCYCLIC COMPOUNDS, OXAZOLE DERIVATIVES, PROCESS FOR PREPARATION OF THE SAME AND USE THEREOF

This application is the National Phase filing of International Patent Application No. PCT/JP02/10326, filed Oct. 3, 2002.

TECHNICAL FIELD

The present invention relates to a heterocyclic compound which is useful as a growth factor receptor tyrosine kinase (particularly HER2) inhibitor, a method for its production, and a pharmaceutical composition containing it.

BACKGROUND

Growth factor and growth factor receptor genes, known as proto-oncogenes, play important roles in the pathology of human tumors such as breast cancer (Aronson et al., Science, Vol. 254, pp. 1146–1153, 1991). Having homology to epidermal growth factor (EGF) receptor, the HER2 (Human EGF receptor-2) gene encodes transmembrane-type glycoprotein, and this receptor possesses tyrosine kinase activity (Akiyama et al., Science, Vol. 232, pp. 1644–1646, 1986). HER2 is found in human breast cancer and ovarian cancer (Slamon et al., Science, Vol. 244, pp. 707–712, 1989) and is also found in prostate cancer (Lyne et al., Proceedings of the American Association for Cancer Research, Vol. 37, p. 243, 1996) and gastric cancer (Yonemura et al., Cancer Research, Vol. 51, p. 1034, 1991). In addition, the substrate for HER2 tyrosine kinase is found in 90% of cases of pancreatic cancer. Transgenic mice incorporating the HER2 gene develop breast cancer as they grow (Guy et al., Proceedings of the National Academy of Science, USA, Vol. 89, pp. 10578–10582, 1992).

An antibody against HER2 was shown to suppress in vitro proliferation of cancer cells (McKenzie et al., Oncogene, Vol. 4, pp. 543–548, 1989); in addition, a human monoclonal antibody against HER2 provided encouraging results in a clinical study in breast cancer patients (Baselga et al., Journal of Clinical Oncology, Vol. 14, pp. 737–744, 1996).

These antibodies interfere with growth factors to bind to HER2 and inhibit the activation of tyrosine kinase. Because these antibodies were thus shown to suppress the progression of cancer in breast cancer patients, drugs which directly inhibit HER2 tyrosine kinase were shown to be potentially effective as therapeutic drugs for breast cancer (Hayes, Journal of Clinical Oncology, Vol. 14, pp. 697–699, 1996).

As a compound that inhibits receptor type tyrosine kinases, including HER2, Japanese Patent Unexamined Publication No. 60571/1999 discloses a compound represented by the formula:

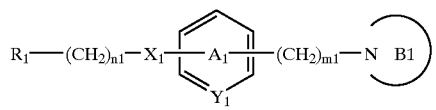

wherein $R_1$ is an aromatic heterocyclic group which may be substituted; $X_1$ is an oxygen atom, an optionally oxidized sulfur atom, —C(=O)— or —CH(OH)—; $Y_1$ is CH or N; m1 is an integer from 0 to 10; n1 is an integer from 1 to 5; the cyclic group:

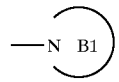

is an aromatic azole group which may be substituted; Ring A1 may be further substituted.

The conventional compounds that inhibit tyrosine kinase are not satisfied as drugs because they have some problems in efficacy, toxicity and the like. And, there is demand for the development of a compound which possesses excellent tyrosine kinase-inhibiting activity, which is of low toxicity, and which is satisfactory as a pharmaceutical.

DISCLOSURE OF INVENTION

The present inventors conducted various investigations on heterocyclic compounds possessing tyrosine kinase-inhibiting activity and succeeded in synthesizing for the first time a compound represented by the formula:

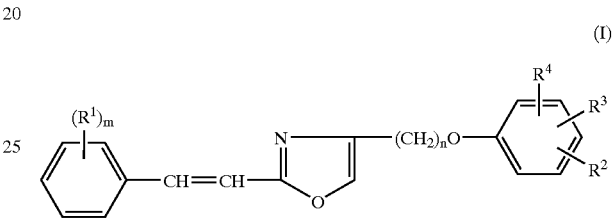

wherein m is an integer of 1 to 3; n is an integer of 1 or 2; $R^1$ is a halogen atom or an optionally halogenated $C_{1-2}$ alkyl group; each of $R^2$ and $R^3$ is, same or different, a hydrogen atom, a halogen atom, a lower alkyl group or a lower alkoxy group; $R^4$ is a group represented by the formula:

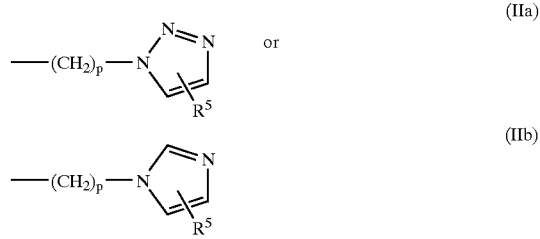

wherein p is an integer of 2 to 5; $R^5$ is a $C_{1-4}$ alkyl group substituted by optionally substituted alkoxycarbonyl group, optionally substituted carbamoyl group, optionally substituted cyclic aminocarbonyl group, optionally substituted carbamoyloxy group, optionally substituted cyclic aminocarbonyloxy group, optionally substituted alkylsulfonyl group, optionally substituted alkylsulfinyl group, optionally substituted sulfamoyl group, optionally substituted cyclic aminosulfonyl group, optionally substituted carbamoylamino group, optionally substituted cyclic aminocarbonylamino group, optionally substituted alkylsulfonylamino group or acylamino group; or a salt thereof and found that the compound or a salt thereof possesses an unexpectedly excellent tyrosine kinase-inhibiting activity based on its unique chemical structure. The inventors conducted further investigations based on this finding and developed the present invention.

Accordingly, the present invention relates to:
(1) A compound represented by the formula (I) or a salt thereof (hereinafter abbreviated as compound (I));
(2) The compound as defined in (1) above, wherein $R^1$ is a halogen atom or trifluoromethyl group, or a salt thereof;

(3) The compound as defined in (1) above, wherein $R^5$ is methylsulfonylethyl group or methylsulfonylmethyl group, or a salt thereof;
(4) The compound as defined in (1) above, wherein both of $R^2$ and $R^3$ are hydrogen atoms, or a salt thereof;
(5) The compound as defined in (1) above, wherein one of $R^2$ and $R^3$ is a hydrogen atom, and the other is methyl group or methoxy group, or a salt thereof;
(6) The compound as defined in (1) above, wherein the compound is N,N-dimethyl-3-[1-(4-(4-[(2-{(E)-2-[4-(trifluoromethyl)phenyl]ethenyl}-1,3-oxazol-4-yl)methoxy]phenyl}butyl)-1H-imidazol-2-yl]propanamide, N-methyl-3-[1-(4-{4-[(2-{(E)-2-[4-trifluoromethyl)phenyl]ethenyl}-1,3-oxazol-4-yl)methoxy]phenyl}butyl)-1H-imidazol-2-yl]propanamide, 2-[(E)-2-(2,4-difluorophenyl)ethenyl]-4-{[4-(4-{2-[2-(methylsulfonyl)ethyl]-1H-imidazol-1-yl}butyl)phenoxy]methyl}-1,3-oxazole, 4-{[4-(4-{2-[(methylsulfonyl)methyl]-1H-imidazol-1-yl}butyl)phenoxy]methyl}-2-{(E)-2-[4-(trifluoromethyl)phenyl]ethenyl}-1,3-oxazole or 4-{[4-(4-{2-[2-(methylsulfonyl)ethyl]-1H-imidazol-1-yl}butyl)phenoxy]methyl}-2-{(E)-2-[4-(trifluoromethyl)phenyl]ethenyl}-1,3-oxazole, or a salt thereof;
(7) A prodrug of the compound as described in (1) above;
(8) A pharmaceutical composition, which comprises the compound as defined in (1) above, or a salt thereof or a prodrug thereof;
(9) The pharmaceutical composition as described in (8) above, which is a tyrosine kinase inhibitor;
(10) The pharmaceutical composition as described in (8) above, which is for preventing or treating cancer;
(11) The pharmaceutical composition as described in (10) above, the cancer is breast cancer, prostate cancer, lung cancer, pancreatic cancer or renal cancer;
(12) A method for inhibiting tyrosine-kinase which comprises administering an effective amount of the compound as defined in (1) above or a salt thereof or a pro-drug thereof to mammals;
(13) A method for preventing or treating cancer which comprises administering an effective amount of the compound as defined in (1) above or a salt thereof or a pro-drug thereof to mammals;
(14) Use of the compound as defined in (1) above or a salt thereof or a pro-drug thereof for preparing a tyrosine kinase inhibitor;
(15) Use of the compound as defined in (1) above or a salt thereof or a pro-drug thereof for preparing an agent for preventing or treating cancer; and the like.
Furthermore, the present invention relates to:
(16) A method for producing a compound represented by the formula:

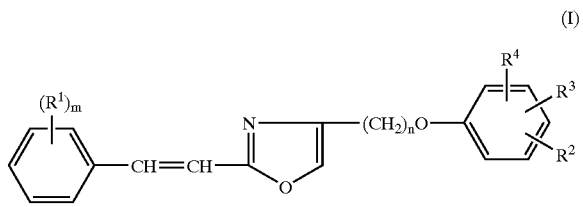

wherein m is an integer of 1 to 3; n is an integer of 1 or 2; $R^1$ is a halogen atom or an optionally halogenated $C_{1-2}$ alkyl group; each of $R^2$ and $R^3$ is, same or different, a hydrogen atom a halogen atom, a lower alkyl group or a lower alkoxy group; $R^4$ is a group represented by the formula:

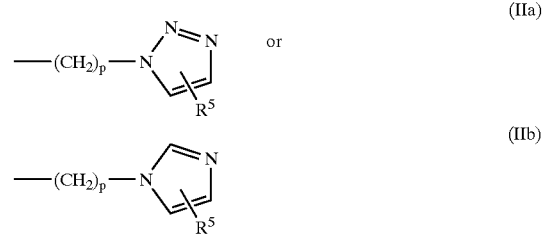

wherein p is an integer of 2 to 5; $R^5$ is a $C_{1-4}$ alkyl group substituted by optionally substituted alkoxycarbonyl group, optionally substituted carbamoyl group, optionally substituted cyclic aminocarbonyl group, optionally substituted carbamoyloxy group, optionally substituted cyclic aminocarbonyloxy group, optionally substituted alkylsulfonyl group, optionally substituted alkylsulfinyl group, optionally substituted sulfamoyl group, optionally substituted cyclic aminosulfonyl group, optionally substituted carbamoylamino group, optionally substituted cyclic aminocarbonylamino group, optionally substituted alkylsulfonylamino group or acylamino group; or a salt thereof comprising reacting a compound represented by the formula:

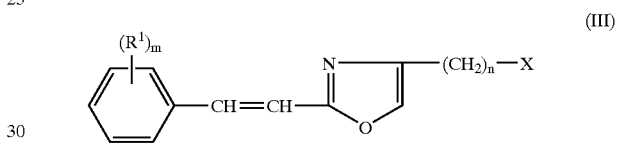

wherein X is a leaving group; the other symbols have the same meanings as defied above, or a salt thereof, with a compound represented by the formula:

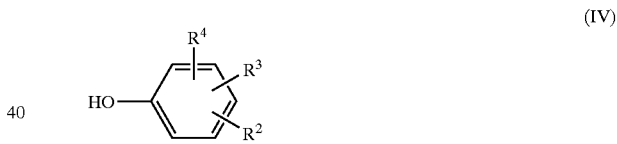

wherein the symbols have the same meanings as defied above, or a salt thereof;
(17) A pharmaceutical composition which combines the compound as defined in (1) above or a salt thereof or a pro-drug thereof and other anti-cancer agents;
(18) A pharmaceutical composition which combines the compound as defined in (1) above or a salt thereof or a pro-drug thereof and hormonal therapeutic agents;
(19) The pharmaceutical composition as defined in (18) above, wherein the hormonal therapeutic agent is a LH-RH modulator;
(20) The pharmaceutical composition as defined in (19) above, wherein the LH-RH modulator is LH-RH agonist;
(21) The pharmaceutical composition as defined in (20) above, wherein the LH-RH agonist is leuprorelin or a salt thereof;
(22) A method for preventing or treating cancer which comprises administering in combination of an effective amount of the compound as defined in (1) above or a salt thereof or a pro-drug thereof and an effective amount of other anti-cancer agents to mammals;
(23) A method for preventing or treating cancer which comprises administering in combination of an effective amount of the compound as defined in (1) above or a salt thereof or a pro-drug thereof and an effective amount of a hormonal therapeutic agent to mammals;

(24) The method as defined in (23) above, wherein the hormonal therapeutic agent is a LH-RH modulator;

(25) The method as defined in (24) above, wherein the LH-RH modulator is LH-RH agonist;

(26) The method as defined in (25) above, wherein the LH-RH agonist is leuprorelin or a salt thereof;

(27) A method for preventing or treating cancer which comprises administering an effective amount of the compound as defined in (1) above or a salt thereof or a pro-drug thereof after administering other anti-cancer agents;

(28) A method for preventing or treating cancer which comprises administering an effective amount of the compound as defined in (1) above or a salt thereof or a pro-drug thereof to mammals before surgery, radiotherapy, genetherapy, thermotherapy, cryotherapy and/or laser cauterization; and

(29) A method for preventing or treating cancer which comprises administering an effective amount of the compound as defined in (1) above or a salt thereof or a pro-drug thereof to mammals after surgery, radiotherapy, genetherapy, thermotherapy, cryotherapy and/or laser cauterization; and the like.

With respect to the formula above, the "halogen atom" represented by $R^1$ is exemplified by fluorine atom, chlorine atom, bromine atom, iodine atom, and the like. In particular, fluorine atom and chlorine atom are preferred.

The "halogen atom" of the "optionally halogenated $C_{1-2}$ alkyl group" represented by $R^1$ is exemplified by fluorine atom, chlorine atom, bromine atom, iodine atom, and the like. In particular, fluorine atom is preferred.

The "$C_{1-2}$ alkyl group" of the "optionally halogenated $C_{1-2}$ alkyl group" represented by $R^1$ is exemplified by methyl group and ethyl group, and methyl is preferred.

Said "$C_{1-2}$ alkyl group" may have 1 to 3, preferably 2 or 3, halogen atoms mentioned above at any possible positions; when 2 or more such halogens are present, they may be identical or different.

As specific examples of said "optionally halogenated $C_{1-2}$ alkyl group", there may be mentioned methyl group, ethyl group, trifluoromethyl group, and the like.

$R^1$ is preferably a halogen atom or a halogenated $C_{1-2}$ alkyl group, and fluorine atom and trifluoromethyl group are more preferable.

When m is 2 or 3, the $R^1$ groups may be identical or different.

The lower alkyl group represented by $R^2$ and $R^3$ is exemplified by $C_{1-6}$ alkyl group such as methyl group, ethyl group, isopropyl group, isobutyl group and the like. In particular, methyl group is preferable. And the lower alkoxy group is exemplified by $C_{1-6}$ alkoxy group such as methoxy group, ethoxy group, and the like. In particular, methoxy group is preferable. The group represented by $R^4$ for the formula:

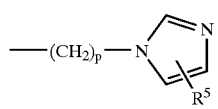

(IIb)

wherein p and $R^5$ have the same meanings as defined above, is preferably a group represented by the formula:

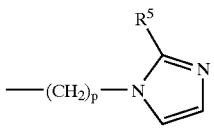

(IIb1)

wherein p and $R^5$ have the same meaning as defined above.

As examples of the "$C_{1-4}$ alkyl group" of the "$C_{1-4}$ alkyl group substituted by optionally substituted alkoxycarbonyl group, optionally substituted carbamoyl group, optionally substituted cyclic aminocarbonyl group, optionally substituted carbamoyloxy group, optionally substituted cyclic aminocarbonyloxy group, optionally substituted alkylsulfonyl group, optionally substituted alkylsulfinyl group, optionally substituted sulfamoyl group, optionally substituted cyclic aminosulfonyl group, optionally substituted carbamoylamino group, optionally substituted cyclic aminocarbonylamino group, optionally substituted alkylsulfonylamino group or acylamino group" represented by $R^5$, there may be mentioned methyl group, ethyl group, propyl group, isopropyl group, butyl group, isobutyl group, sec-butyl group, tert-butyl group, and the like. In particular, methyl group, ethyl group, and the like are preferred.

As examples of said "alkoxycarbonyl group" of the "optionally substituted alkoxycarbonyl group" as a substituent of the "$C_{1-4}$ alkyl group", there may be mentioned $C_{1-4}$ alkoxy carbonyl group such as methoxy carbonyl group, ethoxy carbonyl group, n-propoxy carbonyl group, i-propoxy carbonyl group, n-butoxy carbonyl group, i-butoxy carbonyl group, t-butoxy carbonyl group, and the like. Examples of its substituent are halogen atom, hydroxy group, and the like.

As examples of said "cyclic aminocarbonyl group" of the "optionally substituted cyclic aminocarbonyl group", there may be mentioned piperidinocarbonyl group, morpholinocarbonyl group, piperazinocarbonyl group, and the like. Examples of its substituent are $C_{1-4}$ alkyl group (e.g., methyl group, ethyl group, and the like), $C_{1-4}$ alkoxy group (e.g., methoxy group, ethoxy group, and the like), halogen atom (e.g., fluorine atom, chlorine atom, bromine atom, and the like), hydroxy group, amino group, nitro group, cyano group, oxo group, and the like.

As examples of said "cyclic aminocarbonyloxy group" of the "optionally substituted cyclic aminocarbonyloxy group", there may be mentioned piperidinocarbonyloxy group, morpholinocarbonyloxy group, piperazinocarbonyloxy group, and the like. Examples of its substituent are $C_{1-4}$ alkyl group (e.g., methyl group, ethyl group, and the like), $C_{1-4}$ alkoxy group (e.g., methoxy group, ethoxy group, and the like), halogen atom (e.g., fluorine atom, chlorine atom, bromine atom, and the like), hydroxy group, amino group, nitro group, cyano group, oxo group, and the like.

As examples of said "cyclic aminosulfonyl group" of the "optionally substituted cyclic aminosulfonyl group", there may be mentioned piperidinosulfonyl group, morpholinosulfonyl group, piperazinosulfonyl group, and the like. Examples of its substituent are $C_{1-4}$ alkyl group (e.g., methyl group, ethyl group, and the like), $C_{1-4}$ alkoxy group (e.g., methoxy group, ethoxy group, and the like), halogen atom (e.g., fluorine atom, chlorine atom, bromine atom, and the like), hydroxy group, amino group, nitro group, cyano group, oxo group, and the like.

As examples of said "cyclic aminocarbonylamino group" of the "optionally substituted cyclic aminocarbonylamino group", there may be mentioned piperidinocarbonylamino group, morpholinocarbonylamino group, piperazinocarbonylamino group, and the like. Examples of its substituent are $C_{1-4}$ alkyl group (e.g., methyl group, ethyl group, and the like), $C_{1-4}$ alkoxy group (e.g., methoxy group, ethoxy group, and the like), halogen atom (e.g., fluorine atom, chlorine atom, bromine atom, and the like), hydroxy group, amino group, nitro group, cyano group, oxo group, and the like.

As examples of the substituent of said "optionally substituted alkylsulfonyl group", "optionally substituted alkylsulfinyl group" and "optionally substituted sulfamoyl group", there may be mentioned $C_{1-4}$ alkyl group such as methyl group, ethyl group, and the like; hydroxy-$C_{1-4}$ alkyl group such as hydroxymethyl, hydroxyethyl, and the like; and the like.

As examples of the substituent of said "optionally substituted carbamoyl group", "optionally substituted carbamoyloxy group" and "optionally substituted carbamoylamino group", there may be mentioned $C_{1-4}$ alkyl group such as methyl group, ethyl group; and the like. The "carbamoyl group", "carbamoyloxy group" and "carbamoylamino group" may be mono-substituted or di-substituted.

As examples of "alkyl group" of "optionally substituted alkylsulfonylamino group", there may be mentioned $C_{1-4}$ alkyl group such as methyl group, ethyl group, and the like. The "substituent" is halogen atom such as fluorine atom, chlorine atom, and the like; and the like.

AS examples of "acylamino group", there may be mentioned $C_{2-4}$ alkanoylamino group such as acetylamino group, propionylamino group, and the like; and the like.

The specific examples of $R^5$ are methylcarbamoylethyl group, acetamidoethyl group, methanesulfonylamidoethyl group, methylsulfonylethyl group, methylsulfonylmethyl group, methylsulfinylethyl group, and the like. Especially, methylsulfonylethyl group is preferable.

The preferable examples of compound (I) are the compound represented by the formula:

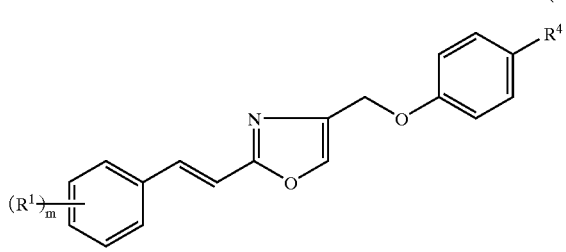

(Ia)

wherein each symbol has the same meaning as defined above, or a salt thereof; or a compound represented by the formula:

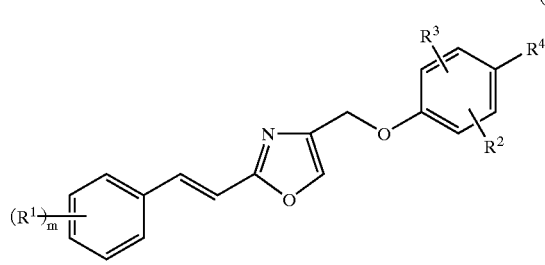

(Ib)

wherein each symbol has the same meaning as defined above, or a salt thereof.

Among compound (I), $R^4$ is preferably a group represented by the formula:

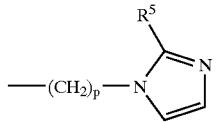

(IIb1)

and especially $R^5$ is preferably methylsulfonylethyl group.

The specific examples of compound (I) are N,N-dimethyl-3-[1-(4-{4-[(2-{(E)-2-[4-(trifluoromethyl)phenyl]ethenyl}-1,3-oxazol-4-yl)methoxy]phenyl}butyl)-1H-imidazol-2-yl]propanamide, N-methyl-3-[1-(4-{4-[(2-{(E)-2-[4-(trifluoromethyl)phenyl]ethenyl}-1,3-oxazol-4-yl)methoxy]phenyl}butyl)-1H-imidazol-2-yl]propanamide, 2-[(E)-2-(2,4-difluorophenyl)ethenyl]-4-{[4-(4-{2-[2-(methylsulfonyl)ethyl]-1H-imidazol-1-yl}butyl)phenoxy]methyl}-1,3-oxazole, 4-{[4-(4-{2-[(methylsulfonyl)methyl]-1H-imidazol-1-yl}butyl)phenoxy]methyl}-2-{(E)-2-[4-(trifluoromethyl)phenyl]ethenyl}-1,3-oxazole, 4-{[4-(4-{2-[2-(methylsulfonyl)ethyl]-1H-imidazol-1-yl}butyl)phenoxy]methyl}-2-{(E)-2-[4-(trifluoromethyl)phenyl]ethenyl}-1,3-oxazole, or a salt thereof, and the like.

As the salt of compound (I) of the present invention, pharmaceutically acceptable salts are preferred, including salts with inorganic bases, salts with organic bases, salts with inorganic acids, salts with organic acids, and salts with basic or acidic amino acids. As preferable examples of salts with inorganic bases, there may be mentioned alkali metal salts such as sodium salt and potassium salt; alkaline earth metal salts such as calcium salt and magnesium salt; aluminum salt; and ammonium salt. As preferable examples of salts with organic bases, there may be mentioned salts with trimethylamine, triethylamine, pyridine, picoline, ethanolamine, diethanolamine, triethanolamine, dicyclohexylamine, N,N'-dibenzylethylenediamine, etc. As preferable examples of salts with inorganic acids, there may be mentioned salts with hydrochloric acid, hydrobromic acid, nitric acid, sulfuric acid, phosphoric acid, etc. As preferable examples of salts with organic acids, there may be mentioned salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. As preferable examples of salts with basic amino acids, there may be mentioned salts with arginine, lysine, ornithine, etc.; as preferable examples of salts with acidic amino acids, there may be mentioned salts with aspartic acid, glutamic acid, etc.

In compound (I), two kinds, i.e., (Z)-ethenyl configuration and (E)-ethenyl configuration, are present; these isomers are included in the scope of the present invention, whether they are present in the form of simple substances or mixtures.

Furthermore, when compound (I) has asymmetric carbons, optical isomers exist; these isomers are included in the scope of the present invention, whether they are present in the form of simple substance or mixtures.

Compound (I) of the present invention or a salt thereof is obtained by commonly known methods, e.g., a method based on the method described in Japanese Patent Unexamined Publication No. 60571/1999, and is also obtained by, for example, the methods schematized by Reaction Formulas A through E below.

The symbols for the compounds given in the schemes for the reaction formulas below have the same definitions as those shown above. The compounds shown in the reaction formulas include salts thereof; examples of such salts include the same salts as those of compound (I).

Reaction Formula A

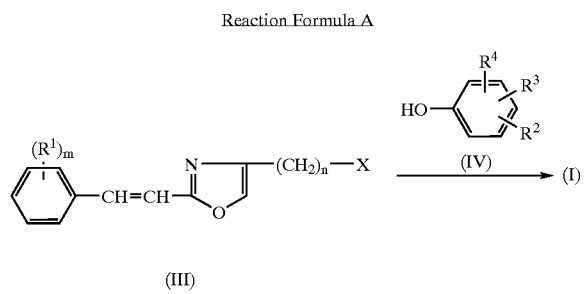

(III)    (IV) → (I)

Reaction Formula B

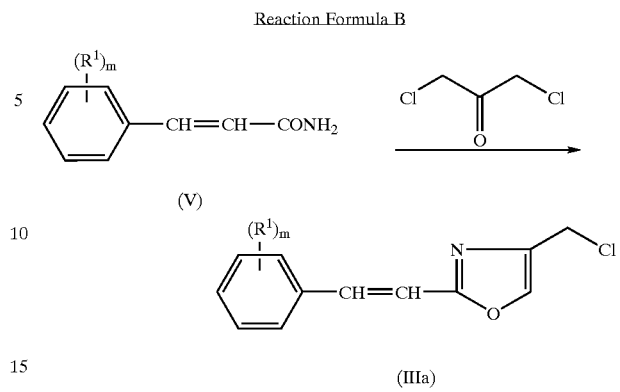

As examples of the "leaving group" represented by X, there may be mentioned halogen atom (e.g., chlorine atom, bromine atom, and the like) or a group represented by the formula: —OSO$_2$R$^6$ wherein R$^6$ is an alkyl group or an aryl group optionally having a substituent.

As examples of the "alkyl group" represented by R$^6$, there may be mentioned C$_{1-6}$ alkyl group such as methyl group, ethyl group, propyl group, and the like.

As examples of the "aryl group" of the "aryl group optionally having a substituent" represented by R$^6$, there may be mentioned C$_{6-14}$ aryl group such as phenyl group.

The "substituent" of the "aryl group optionally having a substituent" represented by R$^6$ is exemplified by C$_{1-6}$ alkyl group such as methyl group, ethyl group, propyl group, and the like.

As specific examples of said "aryl group optionally having a substituent", there may be mentioned phenyl group which may have a C$_{1-6}$ alkyl group (e.g., p-tolyl group).

Compound (III) and compound (IV) are reacted to yield compound (I).

This condensation reaction is usually carried out in the presence of a base between compound (III) and compound (IV).

As examples of said "base," there may be mentioned alkali metal or alkaline earth metal hydroxides (e.g., sodium hydroxide, potassium hydroxide, and the like); alkali metal or alkaline earth metal carbonates (e.g., sodium hydrogen carbonate, sodium carbonate, potassium carbonate, and the like); amines (e.g., pyridine, triethylamine, N,N-dimethylaniline, and the like); alkali metal or alkaline earth metal hydrides (e.g., sodium hydride, potassium hydride, calcium hydride, and the like); alkali metal or alkaline earth metal lower alkoxides (e.g., C$_{1-6}$ alkoxide such as sodium methoxide, sodium ethoxide, potassium tert-butoxide, and the like); and the like.

The amount of "base" used is preferably about 1 to 5 mol per mol of compound (IV).

The amount of "compound (IV)" used is preferably about 0.5 to 5 mol per mol of compound (III).

This reaction is advantageously carried out in the presence of solvent which does not interfere with the reaction. Said solvent is not subject to limitation, as long as the reaction proceeds; as examples of this solvent, aromatic hydrocarbons, ethers, ketones, halogenated hydrocarbons, amides, sulfoxides or mixtures of two or more kinds thereof may be used.

Reaction temperature is normally −50 to +150° C., preferably about −10 to +100° C. Reaction time is normally 0.5 to 48 hours.

Compound (III) can be produced by a commonly known method or a modification thereof, e.g., compound (IIIa), wherein n is 0 and X is chlorine, can be produced by the method shown by Reaction Formula B below, or the like.

Compound (V) and 1,3-dichloroacetone are subjected to a condensation/dehydration reaction to yield compound (IIIa).

If commercially available, compound (V) may be used as a commercial product as is, or may be produced by a commonly known method, a modification thereof, or the like.

The amount of "1,3-dichloroacetone" used is about 1 equivalent to a large excess (amount of solvent) relative to compound (V).

This reaction is advantageously carried out in the absence of solvent or in the presence of solvent which does not interfere with the reaction. Said solvent is not subject to limitation, as long as the reaction proceeds; as examples of this solvent, aromatic hydrocarbons, ethers, ketones, halogenated hydrocarbons or mixtures of two or more kinds thereof may be used.

Reaction temperature is normally 50 to 150° C., preferably about 60 to 120° C. Reaction time is normally 0.5 to 48 hours.

Although the product can be used for the next reaction in the form of a reaction mixture as-is, or in the form of a crude product, it can also be isolated from the reaction mixture by a conventional method.

Compound (IV) can be produced by a commonly known method or a modification thereof, e.g., the method shown by Reaction Formula C below.

Reaction Formula C

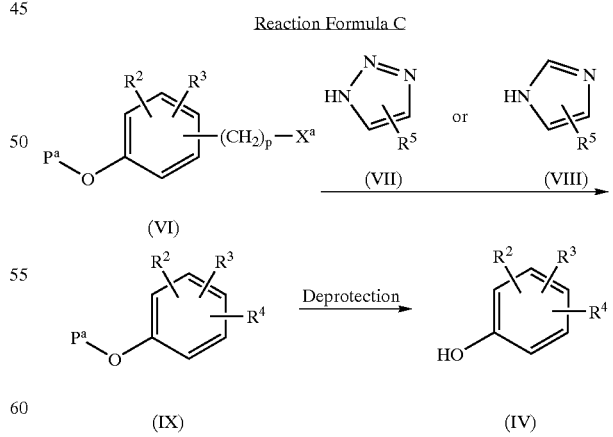

With respect to the formula above, P$^a$ is a hydrogen atom or a protective group; X$^a$ is a leaving group; and other symbols have the same meaning defined above.

As examples of the "protective group" represented by P$^a$, there may be mentioned alkyl group (e.g., C$_{1-6}$ alkyl group such as methyl group, ethyl group, and the like), phenyl-$C_{1-6}$ alkyl group (e.g., benzyl group, and the like), $C_{1-6}$ alkyl-carbonyl group, alkyl-substituted silyl group (e.g., trimethylsilyl group, tert-butyldimethylsilyl group, and the like).

As examples of the "leaving group" represented by $X^a$, there may be mentioned the same examples as those of the "leaving group" represented by X above.

By condensing compound (VI) and compound (VII) or compound (VIII), compound (IX) is obtained as necessary, which is subjected to a deprotecting reaction to give compound (IV).

If commercially available, each of compound (VI), compound (VII) and compound (VIII) may be used as a commercial product as is, or may be produced by a commonly known method, a modification thereof, or the like.

Said "condensation reaction" is normally carried out in the presence of a base in a solvent which does not interfere with the reaction.

Said "base" is exemplified by the bases described in detail with respect to Reaction Formula A above.

The amount of "base" used is preferably about 1 to 5 mol per mol of compound (VI).

The amount of "compound (VII) or compound (VIII)" used is preferably about 0.5 to 5 mol per mol of compound (VI).

Said solvent is not subject to limitation, as long as the reaction proceeds; as examples of this solvent, aromatic hydrocarbons, ethers, ketones, halogenated hydrocarbons, amides, sulfoxides or mixtures of two or more kinds thereof may be used.

The reaction temperature is normally −50 to +150° C., preferably about −10 to +100° C. Reaction time is about 0.5 to 48 hours.

Although compound (IV) obtained can be used for the next reaction in the form of a reaction mixture as-is, or in the form of a crude product, it can also be isolated from the reaction mixture by a conventional method.

Said "deprotection reaction" can be carried out by an appropriately selected conventional method.

When $P^a$ is an alkyl, for example, compound (IX) is subjected to a treatment with an acid (e.g., mineral acid such as hydrobromic acid, and the like; Lewis acid such as titanium tetrachloride, and the like; and the like).

When $P^a$ is a phenyl-$C_{1-6}$ alkyl group, for example, compound (IX) is subjected to a hydrogenation reaction.

When $P^a$ is an alkyl-substituted silyl group, for example, compound (IX) is reacted with a fluoride (e.g., tetrabutylammonium fluoride, and the like).

Although compound (IV) obtained can be used for the next reaction in the form of a reaction mixture as-is, or in the form of a crude product, it can also be isolated from the reaction mixture by a conventional method.

Compound (I) can also be produced by the method shown by Reaction Formula D below.

Reaction Formula D

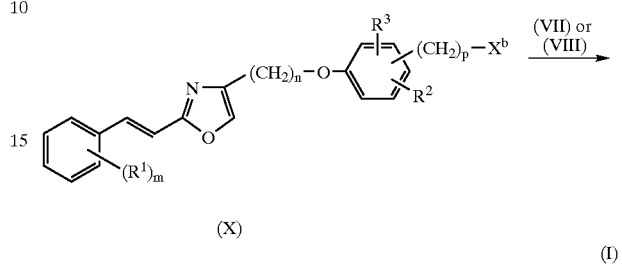

(X)

(I)

With respect to the formula above, $X^b$ is a leaving group.

The "leaving group" represented by $X^b$ is, for example, the same as the leaving group represented by X above.

Compound (X) and compound (VII) or compound (VIII) are reacted to yield compound (I).

This reaction is normally carried out in the presence of a base.

Said "base" is exemplified by the base described in detail with respect to Reaction Formula A above.

The amount of "base" used is preferably about 1 to 5 mol per mol of compound (X).

The amount of each of "compound (VII)" and "compound (VIII)" used is preferably about 0.5 to 5 mol per mol of compound (X).

This reaction is advantageously carried out in the presence of solvent that does not interfere with the reaction. Said solvent is not subject to limitation, as long as the reaction proceeds, and is exemplified by aromatic hydrocarbons, ethers, ketones, halogenated hydrocarbons, amides, sulfoxides, or mixtures of two or more kinds thereof.

The reaction temperature is normally −20 to +150° C., preferably about −10 to +100° C. The reaction time is normally 0.5 to 48 hours.

Of compound (I), compound (Ic), wherein $R^5$ is a carbamoyloxy group, can also be produced by the method shown by Reaction Formula E below.

Reaction Formula E

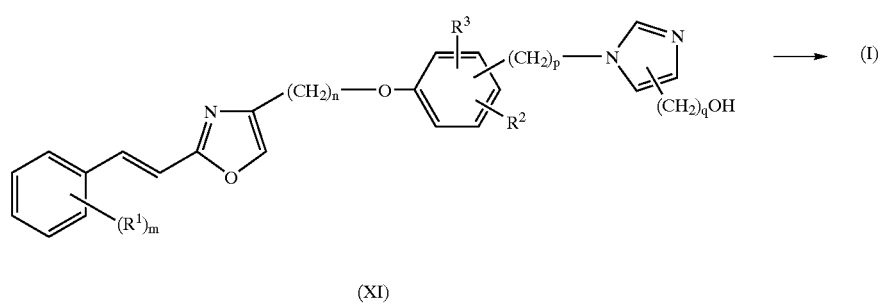

(XI)

Compound (I) can be produced by reacting compound (XI) and corresponding isocyanate.

This reaction is carried out in the absence of a base or in the presence of a base. Said "base" is exemplified by the base described in detail with respect to Reaction Formula A above.

The amount of "base" used is preferably about 1 to 5 mol per mol of compound (XI).

The amount of each of isocyanate used is preferably about 0.5 to 5 mol per mol of compound (XI).

This reaction is advantageously carried out in the presence of solvent that does not interfere with the reaction. Said solvent is not subject to limitation, as long as the reaction proceeds, and is exemplified by aromatic hydrocarbons, ethers, ketones, halogenated hydrocarbons, amides, sulfoxides, or mixtures of two or more kinds thereof.

The reaction temperature is normally −20 to +50° C., preferably about −10 to +20° C. The reaction time is normally 0.1, to 48 hours.

As the aforementioned "aromatic hydrocarbons," for example, benzene, toluene, xylene, etc. are used.

As the aforementioned "ethers," for example, tetrahydrofuran, dioxane, etc. are used.

As the aforementioned "ketones," for example, acetone, 2-butanone, etc. are used.

As the aforementioned "halogenated hydrocarbons," for example, chloroform, dichloromethane, etc. are used.

As the aforementioned "amides," for example, N,N-dimethylformamide etc. are used.

As the aforementioned "sulfoxides," for example, dimethylsulfoxide etc. are used.

In each reaction mentioned above, if the product is obtained as a free form, it can be converted into a salt thereof by a conventional method; if the product is obtained as a salt, it can be converted into a free form thereof by a conventional method.

In the reactions mentioned above, if amino ($NH_2$), hydroxy (OH), carboxyl (COOH), or the like is contained in a substituent, the starting material may have these groups protected and the protective groups may be removed by a commonly known method after the reaction to produce the desired product. As amino-protecting group, there may be mentioned acyl group (e.g., $C_{1-6}$ alkyl-carbonyl group such as acetyl, and the like; benzyloxycarbonyl group; $C_{1-6}$ alkoxy-carbonyl group such as tert-butoxycarbonyl group; phthaloyl group; formyl group; and the like). As examples of hydroxy-protecting group, there may be mentioned $C_{1-6}$ alkyl group (e.g., methyl group, ethyl group, and the like), phenyl-$C_{1-6}$ alkyl group (e.g., benzyl group, and the like), $C_{1-6}$ alkyl-carbonyl group (e.g., acetyl group, and the like), benzoyl group, alkyl-substituted silyl group (e.g., trimethylsilyl group, tert-butyldimethylsilyl group, and the like). As examples of carboxyl-protecting group, there may be mentioned $C_{1-6}$ alkyl group (e.g., methyl group, ethyl group, and the like), phenyl-$C_{1-6}$ alkyl group (e.g., benzyl group, and the like), and the like.

Compound (I) thus obtained can be isolated and purified by commonly known means for separation, e.g., concentration, concentration under reduced pressure, solvent extraction, crystallization, recrystallization, re-dissolution, chromatography, and the like.

If compound (I) is obtained as a free form, it can be converted into a desired salt by a commonly known method or a modification thereof; conversely, if compound (I) is obtained as a salt, it can be converted into a free form or another desired salt by a commonly known method or a modification thereof.

Compound (I) may be a hydrate or a non-hydrate.

When compound (I) is obtained as a mixture of optical isomers, the desired (R)-configuration or (S)-configuration can be separated by a commonly known means of optical resolution.

Compound (I) may be labeled with an isotope (e.g., $^3H$, $^{14}C$) or the like.

A pro-drug of the compound (I) or a salt thereof (hereinafter referred to as the compound (I)) means a compound which is converted to the compound (I) of the present invention with a reaction due to an enzyme, an gastric acid, etc. under the physiological condition in the living body, that is, a compound which is converted to the compound (I) of the present invention with oxidation, reduction, hydrolysis, etc. according to an enzyme; a compound which is converted to the compound (I) of the present invention by hydrolysis etc. due to gastric acid, etc. A prodrug for compound. (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl) methylesterification, cyclohexyloxycarbonylethylesterification and methylamidation, etc.) and the like. Any of these compounds can be produced from compound (I) by a method known per se.

A prodrug for compound (I) may also be one which is converted into compound (I) under a physiological condition, such as those described in. "IYAKUHIN no KAIHATSU (Development of Pharmaceuticals)", Vol.7, Design of Molecules, p. 163–198, Published by HIROKAWA SHOTEN (1990).

The compound (I) of the present invention or a salt thereof or a pro-drug thereof (hereinafter referred to as the compound of the present invention) possesses tyrosine kinase-inhibiting activity and can be used to prevent or treat tyrosine kinase-dependent diseases in mammals. Tyrosine kinase-dependent diseases include diseases characterized by increased cell proliferation due to abnormal tyrosine kinase activity. Furthermore, the compound of the present invention specifically inhibits HER2 tyrosine kinase and is therefore also useful as a therapeutic agent for suppressing the growth of HER2-expressing cancer, or a preventive agent for preventing the transition of hormone-dependent cancer to hormone-independent cancer.

Accordingly, the compound of the present invention can be used as a safe preventive or therapeutic agent for diseases due to abnormal cell proliferation such as various cancers (particularly breast cancer, prostate cancer, pancreatic cancer, gastric cancer, lung cancer, colon cancer, rectal cancer, esophagus cancer, duodenal cancer, cancer of the tongue, cancer of pharynx, cerebral cancer, neurilemoma, non-small cell lung cancer, small cell lung cancer, liver cancer, kidney cancer, cancer of the bile duct, cancer of the uterine body, cancer of the uterine cervix, ovarian cancer, bladder cancer, skin cancer, hemangioma, malignant lymphoma, malignant melanoma, thyroid carcancer, bone tumors, vascular fibroma, retinoblastoma, penile cancer, tumor in childhood, Kaposi's sarcoma, Kaposi's sarcoma derived from AIDS, maxillary tumor, fibrous histiocytoma, leiomyosarcoma, rhabdomyosarcoma, leukemia, etc.), atherosclerosis, angiogenesis (e.g., angiogenesis associated with growth of solid cancer and sarcoma, angiogenesis associated with tumor metastasis, and angiogenesis associated with diabetic nephropathy), and viral diseases (HIV infection etc.).

Tyrosine kinase-dependent diseases further include cardiovascular diseases associated with abnormal tyrosine kinase activity. The compound of the present invention can therefore be used as a preventive or therapeutic agent for cardiovascular diseases such as like re-stenosis.

The compound of the present invention is useful as an anticancer agent for preventing or treating cancers, in particular, breast cancer, prostate cancer, pancreatic cancer, gastric cancer, lung cancer, colonic cancer, carcinoma of the colon and rectum.

The compound of the present invention is of low toxicity and can be used as a pharmaceutical composition as-is, or in a mixture with a commonly known pharmaceutically acceptable carrier etc. in mammals (e.g., humans, horses, bovines, dogs, cats, rats, mice, rabbits, pigs, monkeys, and the like).

In addition to the compound of the present invention, said pharmaceutical composition may contain other active ingredients, e.g., the following hormonal therapeutic agents, anti-cancer agent (e.g., chemotherapy agents, immunotherapy agents, or drugs which inhibit the activity of cell growth factors and receptors thereof), and the like.

As a pharmaceutical for mammals such as humans, the compound of the present invention can be administered orally in the form of, for example, tablets, capsules (including soft capsules and microcapsules), powders, and granules, or non-orally in the form of injections, suppositories, and pellets. Examples of the "parenteral administration route" include intravenous, intramuscular, subcutaneous, intra-tissue, intranasal, intradermal, instillation, intracerebral, intrarectal, intravaginal, intraperitoneal, intratumoral, juxtaposion of tumor and administration directly to the lesion.

The dose of the compound varies depending on the route of administration, symptoms, etc. For example, when it is administered orally as an anticancer agent to a patient (body weight 40 to 80 kg) with breast cancer or prostate cancer, its dose is, for example, 0.5 to 100 mg/kg body weight per day, preferably 1 to 50 mg/kg body weight per day, and more preferably 1 to 25 mg/kg body weight per day. This amount may be administered once or in 2 to 3 divided portions daily.

Desired compound of the present invention can be formulated with a pharmaceutically acceptable carrier and administered orally or non-orally in the form of solid preparations such as tablets, capsules, granules and powders; or liquid preparations such as syrups and injectable preparations.

As pharmaceutically acceptable carriers, there may be used various organic or inorganic carrier substances in common use for pharmaceutical preparations, including excipients, lubricants, binders, and disintegrating agents in solid preparations; solvents, dissolution aids, suspending agents, isotonizing agents, buffers, and soothing agents in liquid preparations. Such pharmaceutical additives as antiseptics, antioxidants, coloring agents, and sweetening agents can also be used as necessary.

As examples of preferable excipients, there may be mentioned, for example, lactose, sucrose, D-mannitol, starch, crystalline cellulose, light silicic anhydride, and the like.

As examples of preferable lubricants, there may be mentioned, for example, magnesium stearate, calcium stearate, talc, colloidal silica, and the like.

As examples of preferable binders, there may be mentioned, for example, crystalline cellulose, sucrose, D-mannitol, dextrin, hydroxypropyl cellulose, hydroxypropylmethyl cellulose, polyvinylpyrrolidone, and the like.

As examples of preferable disintegrating agents, there may be mentioned, for example, starch, carboxymethyl cellulose, carboxymethyl cellulose calcium, crosslinked carmellose sodium, carboxymethyl starch sodium, and the like.

As examples of preferable solvents, there may be mentioned, for example, water for injection, alcohol, propylene glycol, macrogol, sesame oil, corn oil, and the like.

As examples of preferable dissolution aids, there may be mentioned, for example, polyethylene glycol, propylene glycol, D-mannitol, benzyl benzoate, ethanol, trisaminomethane, cholesterol, triethanolamine, sodium carbonate, sodium citrate, and the like.

As examples of preferable suspending agents, there may be mentioned, for example, surfactants such as stearyltriethanolamine, sodium lauryl sulfate, laurylaminopropionic acid, lecithin, benzalkonium chloride, benzetonium chloride, monostearic glycerol, and the like; and hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose, and the like.

As examples of preferable isotonizing agents, there may be mentioned, for example, sodium chloride, glycerol, D-mannitol, and the like.

As examples of preferable buffers, there may be mentioned, for example, buffer solutions of phosphates, acetates, carbonates, citrates, and the like.

As examples of preferable soothing agents, there may be mentioned, for example, benzyl alcohol, and the like.

As examples of preferable antiseptics, there may be mentioned, for example, para-oxybenzoic acid esters, chlorobutanol, benzyl alcohol, phenethyl alcohol, dehydroacetic acid, sorbic acid, and the like.

As examples of preferable antioxidants, there may be mentioned, for example, sulfites, ascorbic acid, and the like.

A pharmaceutical composition can be produced by a conventional method by containing the compound of the present invention in a ratio of normally 0.1 to 95% (w/w) to the total amount of the preparation, although the ratio varies depending on dosage form, method of administration, carrier, etc.

And a combination of (1) administering an effective amount of a compound of the present invention and (2) 1 to 3 selected from the group consisting (i) administering an effective amount of other anti-cancer agents, (ii) administering an effective amount of hormonal therapeutic agents and (iii) non-drug therapy can prevent and/or treat cancer effectively. As the non-drug therapy, for example, surgery, radiotherapy, genetherapy, thermotherapy, cryotherapy, laser cauterization, and the like are exemplified and more than two kinds of these may be combined.

For example, the compound of the present invention can be administered to the same subject simultaneously with other hormonal therapeutic agents, anticancer agent (e.g., chemotherapeutic agents, immunotherapeutic agents, or drugs that inhibit the activity of cell growth factors or cell growth factor receptors)(after here, these are referred to as a combination drug).

Although the compound of the present invention exhibits excellent anticancer action even when used as a simple agent, its effect can be enhanced by using it in combination with one or more of the concomitant drugs mentioned above (multi-agent co-administration).

As examples of said "hormonal therapeutic agents," there may be mentioned fosfestrol, diethylstylbestrol, chlorotrianisene, medtoxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, and the like), pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, epristeride, and the like), adrenocorticohormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), etc. and LH-RH agonists (e.g., goserelin acetate, buserelin, leuprorelin, and the like) are preferable.

As examples of said "chemotherapeutic agents", there may be mentioned alkylating agents, antimetabolites, anticancer antibiotics, plant-derived anticancer agents, and the like.

As examples of "alkylating agents", there may be mentioned nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidiuim hydrochloride, fotemustine, prednimustine, pumitepa, ribomustin, temozolomide, treosuiphan, trophosphamide, zinostatin stimalamer, adozelesin, cystemustine, and bizelesin.

As examples of "antimetabolites", there may be mentioned mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, and the like), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, and ambamustine, etc.

As examples of "anticancer antibiotics", there may be mentioned actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and the like.

As examples of "plant-derived anticancer agents", there may be mentioned etoposide, etoposide phosphate, vinblastine sulfate, vincristine sulfate, vindesine sulfate, teniposide, paclitaxel, docetaxel, vinorelbine, DJ-927, TZT-1027, and the like.

As examples of said "immunotherapeutic agents (BRM)", there may be mentioned picibanil, krestin, sizofiran, lentinan, ubenimex, interferons, interleukins, macrophage colony-stimulating factor, granulocyte colony-stimulating-factor, erythropoietin, lymphotoxin, BCG vaccine, *Corynebacterium parvum*, levamisole, polysaccharide K, procodazole, and the like.

The "cell growth factor" in said "drugs that inhibit the activity of cell growth factors or cell growth factor receptors", there may be mentioned any substances that promote cell proliferation, which are normally peptides having a molecular weight of not more than 20,000 that are capable of exhibiting their activity at low concentrations by binding to a receptor, including (1) EGF (epidermal growth factor) or substances possessing substantially the same activity as it [e.g., EGF, heregulin (HER2 ligand), and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), and the like], and the like.

As examples of said "cell growth factor receptors", there may be mentioned any receptors capable of binding to the aforementioned cell growth factors, including EGF receptor, heregulin receptor (HER2), insulin receptor, IGF receptor, FGF receptor-1 or FGF receptor-2, and the like.

As examples of said "drugs that inhibit the activity of cell growth factor", there may be mentioned trastuzumab (trade mark: Herceptin (anti-HER2 antibody)), gefinitib (EGFR-TKI (epidermal growth factor receptor tyrosine kinase inhibitor)), imatinib mesilate, and the like.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, exatecan, DE-310, and the like), topoisomerase II inhibitors (e.g., sobuzoxane, and the like), differentiation inducers (e.g., retinoid, vitamin D, and the like), angiogenesis inhibitors, α-blockers blockers (e.g., tamsulosin hydrochloride), etc. can be used.

Among those mentioned above, as combination drugs, LH-RH agonists (e.g., goserelin acetate, buserelin, leuprorelin, and the like), trastuzumab (anti-HER2 antibody), etc. are preferable.

In combination of the compound of the present invention and the combination agent of the present invention, the administration time of the compound of the present invention and the combination agent is not restricted, and the compound of the present invention or the combination agent can be administered to an administration subject simultaneously, or may be administered at different times.

The dosage of the combination agent may be determined according to the administration amount clinically used, and can be appropriately selected depending on an administration subject, administration route, disease, combination and the like.

The administration mode of the compound of the present invention and the combination agent of the present invention is not particularly restricted, and it is sufficient that the compound of the present invention and the combination agent are combined in administration. Examples of such administration mode include the following methods:

(1) The compound of the present invention and the combination agent are simultaneously produced to give a single preparation which is administered. (2) The compound of the present invention and the combination agent are separately produced to give two kinds of preparations which are administered simultaneously by the same administration route. (3) The compound of the present invention and the combination agent are separately produced to give two kinds of preparations which are administered by the same administration route only at the different times. (4) The compound of the present invention and the combination agent are separately produced to give two kinds of preparations which are administered simultaneously by the different administration routes. (5) The compound of the present invention and the combination agent are separately produced to give two kinds of preparations which are administered by the different administration routes only at different times (for example, the compound of the present invention and the combination agent are administered in this order, or in the reverse order). After here, these administration modes are referred to as the combination agent of the present invention.

A combination agent of the present invention has low toxicity, and for example, the compound of the present invention or (and) the above-mentioned combination drug can be mixed, according to a method known per se, with a pharmacologically allowable carrier to give pharmaceutical compositions, for example, tablets (including a sugar-coated tablet, film-coated tablet), powders, granules, capsules (including a soft capsule), solutions, injections, suppositories, sustained release agents and the like which can be safely administered orally or parenterally (e.g., local, rectum, vein, and the like). An injection can be administered by intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

As the pharmacologically allowable carrier which may be used in production of the combination agent of the present invention, the same as those for the above mentioned pharmaceutical composition of the present invention can be used.

The compounding ratio of the compound of the present invention to the combination drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to 100% by weight, preferably from about 0.1 to 50% by weight, further preferably from about 0.5 to 20% by weight, based on the preparation.

The content of the combination drug in the combination agent of the present invention differs depending on the form of a preparation, and usually from about 0.01 to 100% by weight, preferably from about 0.1 to 50% by weight, further preferably from about 0.5 to 20% by weight, based on the preparation.

The-content of additives such as a carrier and the like in the combination agent of the present invention differs depending on the form of a preparation, and usually from about 1 to 99.99% by weight, preferably from about 10 to 90% by weight, based on the preparation.

In the case when the compound of the present invention and the combination drug are separately prepared respectively, the same contents may be adopted.

These preparations can be produced by a method known per se usually used in a preparation process.

For example, the compound of the present invention and the combination drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl p-oxybenzoate, benzoic acid, methylparaben, propylparaben, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and prepared into an oily injection, whereby an injection is afforded.

In the case of a preparation for oral administration, an excipient (e.g., lactose, sucrose, starch and the like), a disintegrating agent (e.g., starch, calcium carbonate and the like), a binder (e.g., starch, gum Arabic, carboxymethylcellulose, polyvinylpyrrolidone, hydroxypropylcellulose and the like), a lubricant (e.g., talc, magnesium stearate, polyethylene glycol 6000 and the like) and the like, for example, can be added to the compound of the present invention or the combination drug, according to a method known per se, and the mixture can be compression-molded, then if desirable, the molder product can be coated by a method known per se for the purpose of masking of taste, enteric property or durability, to obtain a preparation for oral administration. As this coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid.acrylic acid copolymer, manufactured by Rohm, DE), pigment (e.g., iron oxide red, titanium dioxide, etc.) and the like can be used. The preparation for oral administration may be any of a quick release preparation and a sustained release preparation.

For example, in the case of a suppository, the compound of the present invention and the combination drug can be made into an oily or aqueous solid, semisolid or liquid suppository according to a method known per se. As the oily substrate used in the above-mentioned composition, for example, glycerides of higher fatty acids [e.g., cacao butter, Witebsols (manufactured by Dynamite Novel, DE), etc.], intermediate grade fatty acids [e.g., Myglyols (manufactured by Dynamite Novel, DE), etc.], or vegetable oils (e.g., sesame oil, soy bean oil, cotton seed oil and the like), and the like are listed. Further, as the aqueous substrate, for example, polyethylene glycols, propylene glycol are listed, and as the aqueous gel substrate, for example, natural gums, cellulose derivatives, vinyl polymers, acrylic acid polymers and the like are listed.

As the above-mentioned sustained release preparation, sustained release microcapsules and the like are listed.

For obtaining a sustained release microcapsule, a method known per se can be adopted, and for example, it is preferably molded into a sustained release preparation shown in the following [2] before administration.

A compound of the present invention is preferably molded into an oral administration preparation such as a solid preparation (e.g., powder, granule, tablet, capsule) and the like, or molded into a rectal administration preparation such as a suppository. Particularly, an oral administration preparation is preferable.

The combination drug can be made into the above-mentioned drug form depending on the kind of the drug.

[1] An injection of the compound of the present invention or the combination drug, and preparation thereof, [2] a sustained release preparation or quick release preparation of the compound of the present invention or the combination drug, and preparation thereof, [3] a sublingual, buccal or intraoral quick integrating agent of the compound of the present invention or the combination drug, and preparation thereof, will be described below specifically.

[1] Injection and Preparation Thereof

An injection prepared by dissolving the compound of the present invention or the combination drug into water is preferable. This injection may be allowed to contain a benzoate and/or salicylate.

The injection is obtained by dissolving the compound of the present invention or the combination drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, organic acid salts such as tromethamol and the like, etc. are listed.

The concentration of the compound of the present invention or the combination drug in an injection is from 0.5 to 50 w/v %, preferably from about 3 to 20 w/v %. The concentration of a benzoate or/and salicylate is from 0.5 to 50 w/v %, preferably from 3 to 20 w/v %.

Into a preparation of the present invention, additives usually used in an injection, for example, a stabilizer (ascorbic acid, sodium pyrosulfite, and the like), a surfactant (Polysorbate 80, macrogol and the like), a solubilizer (glycerin, ethanol and the like), a buffer (phosphoric acid and alkali metal salt thereof, citric acid and alkali metal salt thereof, and the like), an isotonizing agent (sodium chloride, potassium chloride, and the like), a dispersing agent (hydroxypropylmethylcellulose, dextrin), a pH regulator (hydrochloric acid, sodium hydroxide and the like), a preservative (ethyl p-oxybenzoate, benzoic acid and the like), a dissolving agent (conc. glycerin, meglumine and the like), a dissolution aid (propylene glycol, sucrose and the like), a soothing agent (glucose, benzyl alcohol and the like), and the like, can be appropriately blended. These additives are generally blended in a proportion usually used in an injection.

It is advantageous that pH of an injection is controlled from 2 to 12, preferably from 2.5 to 8.0 by addition of a pH regulator.

An injection is obtained by dissolving the compound of the present invention or the combination drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously be heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 minutes.

Further, a preparation endowed with an antibacterial property of a solution may also be produced so that it can be used as a preparation which is divided and administered multiple-times.

[2] Sustained Release Preparation or Quick Release Preparation, and Preparation Thereof A sustained release preparation is preferable which is obtained, if desirable, by coating a nucleus containing the compound of the present invention or the combination drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudoragits (Rohm Farma) such as Eudoragit RS-100, RL-100, RS-30D, RL-30D, RL-PO, RS-PO (ethyl acrylate.methyl methacrylate·trimethyl chloride methacrylate.ammonium-ethyl copolymer), Eudoragit NE-30D (methyl methacrylate.ethyl acrylate copolymer), and the like, hardened oils such as hardened castor oil (e.g., Lovery wax (Freunt) and the like), waxes such as carnauba wax, fatty acid glycerin ester, paraffin and the like, polyglycerin fatty esters, and the like.

As the swellable polymer, polymers having an acidic dissociating group and showing pH dependent swell are preferable, and polymers manifesting small swelling in acidic regions such as in stomach and large swelling in neutral regions such as in small intestine and large intestine are preferable.

As such a polymer having an acidic dissociating group and showing pH dependent swell, cross-linkable polyacrylic acid copolymers such as, for example, Carbomer 934P, 940, 941, 974P, 980, 1342 and the like, polycarbophil, calcium polycarbophil (last two are manufactured by BF good rich), Hibiswako 103, 104, 105, 304 (all are manufactured by Wako Purechemical Co., Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl group or carboxyalkyl group such as hydroxypropylcellulose, hydroxypropylmethylcellulose, carboxymethylcellulose sodium and the like, methylcellulose, polyvinylpyrrolidone, polyvinyl alcohol, polyethylene glycol and the like can be mentioned.

The content of a water-insoluble substance in the film agent of a sustained release preparation is from about 30 to 90% (w/w), preferably from about 35 to 80% (w/w), further preferably from about 40 to 75% (w/w), the content of a swellable polymer is from about 3 to 30% (w/w), preferably from about 3 to 15% (w/w). The film agent may further contain a hydrophilic substance, and in which case, the content of a hydrophilic substance in the film agent is about 50% (w/w) or less, preferably about 5 to 40% (w/w), further preferably from about 5 to 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to 2000 μm, further preferably, from about 500 to 1400 μm.

Preparation of the nucleus can be effected by a usual production method. For example, a suitable excipient, binding agent, disintegrating agent, lubricant, stabilizer and the like are mixed into a drug, and the mixture is subjected to a wet extrusion granulating method, fluidized bed granulating method or the like, to prepare a nucleus.

The content of drugs in a nucleus is from about 0.5 to 95% (w/w), preferably from about 5.0 to 80% (w/w), further preferably from about 30 to 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropyl cellulose, polyethylene glycol, polyvinyl pyrrolidone, Pluronic F68, gum Arabic, gelatin, starch and the like are used. As the disintegrating agent, for example, carboxymethylcelulose calcium (ECG505), crosscarmelose sodium (Ac-Di-Sol), crosslinked polyvinylpyrrolidone (Crosspovidone), lower substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose, waxes can be used, and the average particle size thereof is preferably from about 100 μm to 1500 μm.

For separating a drug and a film agent contained in a nucleus, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl group or carboxyalkyl group are used, more preferably, hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to 15% (w/w), preferably from about 1 to 10% (w/w), further preferably from about 2 to 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus With Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to 90% (w/w), preferably from about 5 to 50% (w/w), further preferably from about 5 to 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hardened castor oil, triethyl citrate, cetyl alcohol, stearyl alcohol and the like may also be added as a plasticizer.

After coating with a film agent, if necessary, an antistatic agent such as talc and the like may be mixed.

The quick release preparation may be liquid (solution, suspension, emulsion and the like) or solid (particle, pill, tablet and the like). Oral agents and parenteral agents such as an injection and the like are used, and oral agents are preferable.

The quick release preparation, usually, may contain, in addition to an active component drug, also carriers, additives and excipients conventionally used in the production field (hereinafter, sometimes abbreviated as excipient). The preparation excipient used is not particularly restricted providing it is an excipient ordinarily used as a preparation excipient. For example, as the excipient for an oral solid preparation, lactose, starch, corn starch, crystalline cellulose (Acevil PH101, manufactured by Asahi Chemical Industry Co., Ltd., and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to 99.4 w/w %, preferably from about 20 to 98.5 w/w %, further preferably from about 30 to 97 w/w %, based on the total amount of the quick release preparation.

The content of a drug in the quick release preparation can be appropriately selected in the range from about 0.5 to 95%, preferably from about 1 to 60% based on the total amount of the quick release preparation.

When the quick release preparation is an oral solid preparation, it usually contains, in addition to the above-mentioned components, also an integrating agent. As this integrating agent, for example, carboxymethylcellulose calcium (ECG-505, manufactured by Gotoku Yakuhin), cross-carmelose sodium (for example, Actisol, manufactured by Asahi Chemical Industry Co., Ltd.), crosspovidone (for example, Colicone CL, manufactured by BASF), lower substitution hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially pregelatinized starch (PCS, manufactured by Asahi Chemical Industry Co., Ltd.), and the like are used, and for example, those which disintegrate a granule by adsorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and blending amount of a drug used, design of releasing property, and the like, and for example, from about 0.05 to 30 w/w %, preferably from about 0.5 to 15 w/w %, based on the total amount of the quick releasing agent.

When the quick release preparation is an oral solid preparation, it may further contain, in addition to the above-mentioned composition in the case of the oral solid preparation, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxylmethylcellulose, polybinylpyrrolidone, pluran, dextrin and the like), a lubricant (e.g., polyethylene glycol, magnesium stearate, talc, light anhydrous silicic acid (for example, aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene cartor oil derivatives and the like), a coloring agent (e.g., tar coloring matter, caramel, iron oxide red, titanium oxide, riboflavins), if necessary, an appetizing agent (e.g., sweetening agent, arom and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The quick releasing reparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a quick release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Pulek), and the like, and then, granulating the mixture by a wet extrusion granulation method, fluidized bed granulation method and the like.

Thus obtained quick releasing preparation and sustained releasing preparation may be themselves made into products or made into products appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation appropriately together with preparation excipients and the like. It may also be permissible that they are made into granules or fine particles, and filled in the same capsule to be used as a preparation for oral administration.

[3] Sublinguial, Buccal or Intraoral Quick Disintegrating Agent and Preparation Thereof Sublinguial, buccal or intraoral quick disintegrating agents may be a solid preparation such as tablet and the like, or may be an oral mucosa membrane patch (film).

As the sublinguial, buccal or intraoral quick disintegrating agent, a preparation containing the compound of the present invention or the combination drug and an excipient is preferable. It may contain also auxiliary agents such as a lubricant, isotonizing agent, hydrophilic carrier, water-dispersible polymer, stabilizer and the like. Further, for easy absorption and increase in in vivo use efficiency, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., fine crystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbofil, ascorbate palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublinguial, buccal or intraoral quick disintegrating agent can be produced by mixing the compound of the present invention or the combination drug and an excipient by a method known per se. Further, if desired, auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the combination drug and the above-mentioned water-dispersible polymer (preferably, hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbofil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into given area.

As the preferable intraoral quick disintegrating agent, there are listed solid quick scattering dose agents composed of a network body comprising the compound of the present invention or the combination drug, and a water-soluble or water-diffusible carrier which is inert to the compound of the present invention or combination drug, are listed. This network body is obtained by sublimating a solvent from the solid composition constituted of a solution prepared by dissolving the compound of the present invention or the combination drug in a suitable solvent.

It is preferable that the composition of an intraoral quick disintegrating agent contains a matrix forming agent and a secondary component, in addition to the compound of the present invention or the combination drug.

Examples of the matrix forming agent include animal proteins or vegetable proteins such as gelatins, dextrins, soybean, wheat and psyllium seed protein and the like; rubber substances such as gum Arabic, guar gum, agar, xathane gum and the like; polysaccharides; alginic acids; carboxymethylcelluloses; caragenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the combination drug in the solution or suspension in diffused condition, in addition to formation of the matrix.

The composition may contain secondary components such as a preservative, antioxidant, surfactant, thickening agent, coloring agent, pH controlling agent, flavoring agent, sweetening agent, food taste masking agent and the like. As the suitable coloring agent, there are listed red, black and yellow iron oxides, and FD & C dyes such as FD & C Blue 2, FD & C Red 40 and the like manufactured by Elis and Eberald. Examples of the suitable flavoring agent include mint, raspberry, licorice, orange, lemon, grape fruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the combination drug in an amount usually from about 0.1 to 50% by weight, preferably from about 0.1 to 30% by weight, and preferable are preparations (such as the above-mentioned sublingual agent, buccal and the like) which can dissolve 90% or more of the compound of the present invention or the combination drug (into water) within the time range of about 1 to 60 minutes, preferably of about 1 to 15 minutes, more preferably of about 2 to 5 minutes, and intraoral quick disintegrating preparations which are disintegrated within the range of 1 to 60 seconds, preferably of 1 to 30 seconds, further preferably of 1 to 10 seconds after place in an oral cavity.

The content of the above-mentioned excipient in the whole preparation is from about 10 to 99% by weight, preferably from about 30 to 90% by weight. The content of β-cyclodextrin or β-cyclodextrin derivative in the whole preparation is from 0 to about 30% by weight. The content of the lubricant in the whole preparation is from about 0.01 to 10% by weight, preferably from about 1 to 5% by weight. The content of the isotonizing agent in the whole preparation is from about 0.1 to 90% by weight, preferably, from about 10 to 70% by weight. The content of the hydrophilic carrier in the whole preparation is from about 0.1 to 50% by weight, preferably, from about 10 to 30% by weight. The content of the water-dispersible polymer in the whole preparation is from about 0.1 to 30% by weight, preferably, from about 10 to 25% by weight. The content of the stabilizer in the whole preparation is from about 0.1 to 10% by weight, preferably, from about 1 to 5% by weight. The above-mentioned preparation may further contain additives such as a coloring agent, sweetening agent, preservative and the like, if necessary.

The dosage of a combination agent of the present invention differs depending on the kind of a compound of the present invention, age, body weight, condition, drug form, administration method, administration period and the like, and for example, for one breast cancer patient (adult, body weight: about 60 kg), the combination agent is administered intravenously, at a dose of about 0.01 to 1000 mg/kg/day, preferably about 0.01 to 100 mg/kg/day, more preferably about 0.1 to 100 mg/kg/day, particularly about 0.1 to 50 mg/kg/day, especially about 1.5 to 30 mg/kg/day, in terms of the compound of the present invention or the combination drug, respectively, once or several time in division a day. Of course, since the dose as described above varies depending on various conditions, amounts smaller than the above-mentioned dosage may sometimes be sufficient, further, amounts over that range sometimes have to be administered.

The amount of the combination drug can be set at any value unless side effects are problematical. The daily dosage in terms of the combination drug differs depending on the severity of the symptom, age, sex, body weight, sensitivity difference of the subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times in division a day.

In administration of a combination agent of the present invention, the compound of the present invention may be administered after administration of the combination drug or the combination drug may be administered after administration of the compound of the present invention, though they may be administered simultaneously. When administered at a time interval, the interval differs depending on the effective ingredient to be administered, drug form and administration method, and for example, when the combination drug is administered first, a method in which the compound of the present invention is administered within time range of from 1 minute to 3 days, preferably from 10 minutes to 1 day, more preferably from 15 minutes to 1 hour after administration of the combination drug is exemplified. When the compound of the present invention is administered first, a method in which the combination drug is administered within time range of from 1 minute to 1 day, preferably from 10 minutes to 6 hours, more preferably from 15 minutes to 1 hour after administration of the compound of the present invention is exemplified.

In a preferable administration method, for example, the combination drug which has been formed into an oral administration preparation is administered orally at a daily dose of about 0.001 to 200 mg/kg, and about 15 minutes after, the compound of the present invention which has been formed into an oral administration preparation is administered orally at a daily dose of about 0.005 to 100 mg/kg.

In addition, the pharmaceutical composition of the present invention and the combined agent of the present invention can be combined with a non-drug therapy such as (1) surgery, (2) hypertensive chemotherapy using angiotensin II etc., (3) genetherapy, (4) thermotherapy, (5) cryotherapy, (6) laser cauterization, (7) radiotherapy, etc.

For example, the pharmaceutical composition of the present invention and the combined agent of the present invention inhibits an expression of resistance, extends disease-free survival, suppresses cancer metastasis or recurrence, prolongs survival and provides other benefits when used before or after the surgery, etc., or a combination treatment comprising 2 or 3 of these therapies.

Also, treatment with the pharmaceutical composition of the present invention and the combined agent of the present invention can be combined with supportive therapies [e.g., (i) administration of antibiotics (e.g., β-lactams such as pansporin, macrolides such as clarytheromycin) to an combined expression of various infectious diseases, (ii) administration of total parentral nutrition, amino acid preparations and general vitamin preparations for improvement of malnutrition, (iii) morphine administration for pain mitigation, (iv) administration of drugs which mitigate adverse reactions such as nausea, vomiting, anorexia, diarrhea, leukopenia, thrombocytopenia, hemoglobin concentration reduction, hair loss, hepatopathy, renopathy, DIC and fever, (v) administration of drugs for inhibition of multiple drug resistance in cancer, and the like].

Preferably, the pharmaceutical composition of the present invention or the combined agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the pharmaceutical composition of the present invention or the combined agent of the present invention before the surgery, etc., for example, it can be administrated 1-time about 30 minutes to 24 hours before the surgery, etc., or in 1 to 3 cycles about 3 months to 6 months before the surgery, etc. In this way, the surgery, etc. can be conducted easily because, for example, a cancer tissue would be reduced by administering the pharmaceutical composition of the present invention or the combined agent of the present invention before the surgery, etc.

As a period for administering the pharmaceutical composition of the present invention or the combined agent of the present invention after the surgery, etc., for example, it can be administrated repeatedly per a few weeks to 3 months, about 30 minutes to 24 hours after the surgery, etc. In this way, it makes an effect of the surgery, etc. increasing by administering the pharmaceutical composition of the present invention or the combined agent of the present invention after the surgery, etc.

EXAMPLES

The present invention is hereinafter described in detail by means of, but is not limited to, the following reference examples, examples, preparation examples and test examples.

In the reference examples and examples, column chromatography was conducted with observation by TLC (thin layer chromatography). In TLC observation, the TLC plate used was the Merck Kieselgel 60$F_{254}$ plate, the developing solvent used was the solvent used as the eluent for column chromatography, and the means of detection used was an UV detector. The silica gel for the column chromatography was also Merck Kieselgel 60$F_{254}$ (70–230 mesh). NMR spectra are shown by proton NMR with tetramethylsilane as the internal standard, using VARIAN Gemini-200 (200 MHz type spectrometer); δ values are expressed in ppm.

The abbreviations used in the reference examples and examples are defined as follows:
s: Singlet
br: Broad
d: Doublet
t: Triplet
q: Quartet
dd: Double doublet
dt: Double triplet
m: Multiplet
J: Coupling constant
Hz: Hertz
DMF: N,N-dimethylformamide
THF: Tetrahydrofuran Reference Example 1

4-chloromethyl-2-[(E)-2-(4-trifluoromethylphenyl) ethenyl]-1,3-oxazole

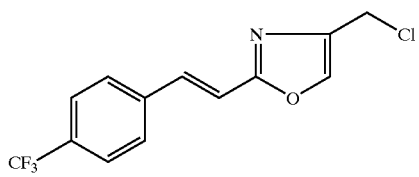

(i) (E)-3-(4-trifluoromethylphenyl)-2-propenamide

To a suspension of 4-trifluoromethylcinnamic acid (19.4 g), and DMF (6 drops) in THF (100 ml), oxalyl chloride (11.7 ml) was added at 0° C., followed by stirring at room temperature for 2 hours. The solvent was evaporated under reduced pressure. The residue was dissolved in ethyl acetate (60 ml) and poured into a mixture of 25% aqueous ammonia-ethyl acetate (5:1, 120 ml). The water layer was salted out; the organic layer was extracted with ethyl acetate-THF (12:1, 650 ml) and ethyl acetate (100 ml×2). The extract was dried over magnesium sulfate, after which it was concentrated under reduced pressure. The residue was recrystallized from ethyl acetate-hexane to give the titled compound (18.0 g) as colorless plate crystals.

$^1$H-NMR (CDCl$_3$) δ: 5.58 (2H, br s), 6.53 (1H, d, J=15.8 Hz), 7.63–7.72 (5H, m). IR (KBr): 3326, 3167, 1686, 1636, 1617, 1404, 1190 cm$^{-1}$.

(ii) 4-chloromethyl-2-[(E)-2-(4-trifluoromethylphenyl)ethenyl]-1,3-oxazole

A mixture of (E)-3-(4-trifluoromethylphenyl)-2-propenamide (17.9 g) and 1,3-dichloroacetone (14.8 g) in toluene (83 ml) was refluxed for 9 hours by use of Dean-Stark apparatus. After cooling, the reaction mixture was combined with water, extracted with ethyl acetate, washed with saturated brine, and dried over magnesium sulfate, then concentrated under reduced pressure. The residue was purified by silica gel column chromatography (eluent: hexane-:ethyl acetate=6:1 to 5:1) to give the titled compound (15.1 g) as colorless needle crystals.

$^1$H-NMR (CDCl$_3$) δ: 4.55 (2H, d, J=0.8 Hz), 7.00 (1H, d, J=16.2 Hz), 7.56 (1H, d, J=16.2 Hz), 7.64–7.68 (5H, m). IR (KBr): 1350, 1325, 1170, 1136, 1113, 1071, 959, 826, 727, 708 cm$^{-1}$.

Reference Example 2

4-chloromethyl-2-[(E)-2-(2,4-difluorophenyl) ethenyl]-1,3-oxazole

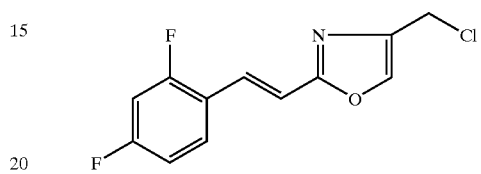

Using (E)-3-(2,4-difluorophenyl)-2-propenamide (9.16 g) and 1,3-dichloroacetone (7.62 g), the same reaction as Reference Example 1-(ii) was carried out to yield the titled compound (6.31 g) as colorless crystals.

$^1$H-NMR (CDCl$_3$) δ: 4.55 (2H, s), 6.8–7.0 (2H, m), 6.96 (1H, d, J=16.8), 7.45–7.7 (3H, m).

Reference Example 3

4-chloromethyl-2-[(E)-2-(2,6-difluorophenyl) ethenyl]-1,3-oxazole

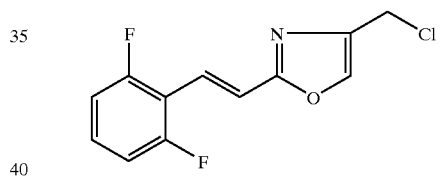

Using (E)-(2,6-difluorophenyl)-2-propenamide (9.0 g) and 1,3-dichloroacetone (7.49 g), the same reaction as Reference-Example 1-(ii) was carried out to yield the titled compound (7.18 g) as a light-yellow solid.

$^1$H-NMR (CDCl$_3$) δ: 4.55 (2H, s), 6.85–7.0 (2H, m), 7.2–7.35 (2H, m), 7.55–7.7 (1H, m), 7.66 (1H, s).

Reference Example 4

4-{4-[2-(2-hydroxyethyl)-1H-imidazol-1-yl] butyl}phenol

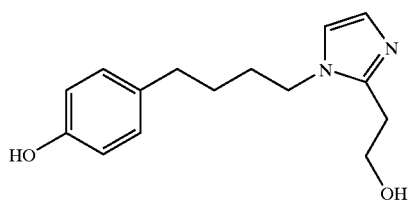

(i) 2-(1-{4-[4-(benzyloxy)phenyl]butyl}-1H-imidazol-2-yl)-1-ethanol

Benzyl 4-(4-iodobutyl)phenyl ether (14.29 g), 2-(2-hydroxyethyl)imidazole (13.1 g) and potassium carbonate (5.39 g) were stirred in DMF (390 ml) at 60° C. for 16 hours. After cooling, the insoluble matter was filtered off; the filtrate was concentrated under reduced pressure. The residue was dissolved in ethyl acetate and washed with water and saturated brine. Under reduced pressure, the solvent was distilled off; the residue was purified by column chromatography (eluent:ethyl acetate:methanol=19:1 to 9:1). The eluate was recrystallized from ethyl acetate-methanol to give the titled compound (10.99 g) as colorless crystals.

mp 75–77° C. $^1$H-NMR (CDCl$_3$) δ: 1.53–1.82 (4H, m), 2.58 (2H, t, J=7.1 Hz), 2.78 (2H, t, J=5.5 Hz), 3.81 (2H, t, J=6.9 Hz), 4.03 (2H, t, J=5.5 Hz), 5.04 (2H, s), 6.80 (1H, d, J=1.2 Hz), 6.90 (2H, d, J=8.6 Hz), 6.93 (1H, d, J=1.2 Hz), 7.05 (2H, d, J=8.6 Hz), 7.34–7.47 (5H, m). IR (KBr): 3144, 3032, 2934, 2859, 1611, 1582, 1514, 1495, 1456, 1431, 1381, 1298, 1273, 1244, 1175, 1150, 1121, 1109, 1051, 1026 cm$^{-1}$.

(ii) 4-{4-[2-(2-hydroxyethyl)-1H-imidazol-1-yl]butyl}phenol

Using 2-(1-{4-[4-(benzyloxy)phenyl]butyl}-1H-imidazol-2-yl)-1-ethanol (10.67 g) and 10% palladium carbon (1.6 g), the same reaction as Reference Example 11-(v) was carried out to yield the titled compound (5.3 g).

mp 118–119° C. $^1$H-NMR (CDCl$_3$) δ: 1.50–1.80 (4H, m), 2.55 (2H, t, J=7.0 Hz), 2.79 (2H, t, J=5.8 Hz), 3.82 (2H, t, J=7.0 Hz), 3.97 (2H, t, J=5.8 Hz), 3.85–4.40 (1H, br), 6.77 (2H, d, J=8.4 Hz), 6.80 (1H, s), 6.94 (1H, s), 6.96 (2H, d, J=8.4 Hz). IR (KBr): 3600–2400, 1615, 1593, 1516, 1489, 1456, 1373, 1252, 1171, 1150, 1125, 1103, 1055 cm$^{-1}$.

Reference Example 5

2-[1-[4-[4-[2-[(E)-2-(4-trifluoromethylphenyl)ethenyl]oxazol-4-yl]methoxyphenyl]butyl-1H-imidazol-2-yl]-1-ethanol

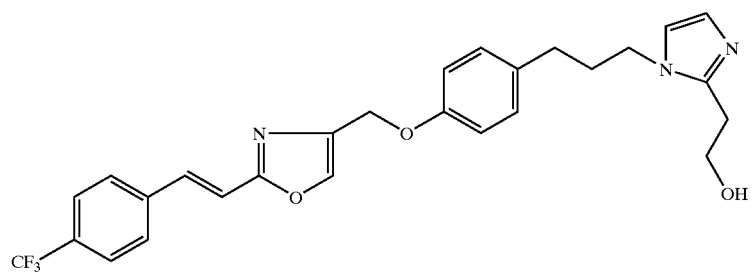

Under argon atmosphere, DMF (4 ml) was added to a mixture of 65% sodium hydride (40.6 mg) and 4-[4-[2-(2-hydroxyethyl)-1H-imidazol-1-yl]butyl]phenol (260 mg) at 0° C. The mixture was stirred at room temperature for 30 min. [2-[(E)-2-(4-Trifluoromethylphenyl)ethenyl]oxazol-4-yl]methyl chloride (316 mg) was added to the mixture at 0° C., and the mixture was stirred at room temperature for 15 hr. Water was added to the mixture to give crystals. The crystals were collected by filtration, washed with water and isopropyl ether and recrystallized from acetone-hexane to give the titled compound (393 mg) as pale yellow needle crystals.

$^1$H-NMR (CDCl$_3$) δ: 1.56–1.74 (4H, m), 2.59 (2H, t, J=6.6 Hz), 2.78 (2H, t, J=5.4 Hz), 3.82 (2H, t, J=6.8 Hz), 4.03 (2H, t, J=5.4 Hz), 5.02 (2H, d, J=1.2 Hz), 6.81 (1H, d, J=1.6 Hz), 6.90–6.95 (4H, m), 7.02 (2H, d, J=16.2 Hz), 7.52–7.69 (6H, m). IR (KBr): 1512, 1323, 1244. 1175, 1132, 1113, 1067, 1055 cm$^{-1}$.

Reference Example 6

Production of 4-[4-[2-[2-(methylsulfanyl)ethyl]-1H-imidazol-1-yl]butyl]phenol

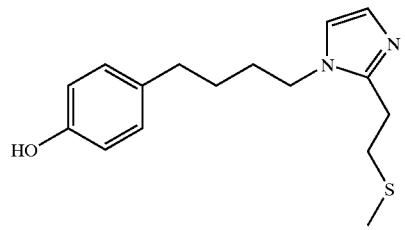

(i) Production of 1-tert-butoxy-4-(4-iodobutyl)benzene

Triethylamine (32.9 ml) and methanesulfonyl chloride (14.6 ml) were added to a solution of 4-(4-tert-butoxyphenyl)butan-1-ol (35.0 g) in ethyl acetate (360 ml) at 0° C., and the mixture was stirred at 0° C. for 1.5 hr. By adding water, the reaction mixture was separated. The organic layer was washed successively with 5% sodium hydrogen carbonate solution and water and dried over anhydrous magnesium sulfate. The solvent was evaporated under reduced pressure to give crude 4-(4-tert-butoxyphenyl)butyl methanesulfonate (50.2 g). A suspension of the product (50.2 g) and sodium iodide (46.1 g) in acetone (500 ml) was stirred for 4.5 hr. By adding water and diisopropyl ether, the reaction mixture was separated. The organic layer was successively washed with 10% hypowater and water, dried over anhydrous magnesium sulfate. The solvent was evaporated under reduced pressure to give the titled compound (52.1 g) as a colorless oil.

$^1$H-NMR (CDCl$_3$) δ: 1.33 (9H, s), 1.60–1.70 (2H, m), 1.80–1.90 (2H, m), 2.59 (2H, t, J=7.5 Hz), 3.20 (2H, t, J=6.9 Hz), 6.90 (2H, d, J=8.4 Hz), 7.04 (2H, d, J=8.4 Hz).

(ii) Production of 2-[1-[4-(4-tert-butoxyphenyl)butyl]-1H-imidazol-2-yl]ethanol

65% sodium hydride (1.78 g) was added to a solution of 2-(1H-imidazol-2-yl)ethanol (5.62 g) in DMF (80 ml) at 0° C., and the mixture was stirred at room temperature for 30 min. A solution of 1-tert-butoxy-4-(4-iodobutyl)benzene (13.3 g) in DMF (20 ml) was added to the mixture at 0° C., and the mixture was stirred at the same temperature for 5 hr. The reaction mixture was combined with water and extracted with ethyl acetate. The extract was washed successively with water (twice), and saturated brine, dried over anhydrous magnesium sulfate. The solvent was evaporated under reduced pressure, and the residue was purified by silica gel column chromatography (Chromatorex; eluent hexane:ethyl acetate=2:5) to give the titled compound (9.53 g) as a colorless amorphous form.

¹H-NMR (CDCl₃) δ: 1.33 (9H, s), 1.53–1.82 (4H, m), 2.59 (2H, t, J=7.0 Hz), 2.78 (2H, t, J=5.4 Hz), 3.82 (2H, t, J=7.0 Hz), 4.03 (2H, t, J=5.4 Hz), 4.49 (1H, br s), 6.80 (1H, d, J=1.4 Hz), 6.86–6.93 (3H, m), 6.99–7.05 (2H, m). IR (KBr): 2976, 1507, 1366, 1235, 1163 cm⁻¹.

(iii) Production of tert-butyl 4-[4-[2-[2-(methylsulfanyl)ethyl]-1H-imidazol-1-yl]butyl] phenyl Ether Triethylamine (3.16 ml) and methanesulfonyl chloride (1.40 ml) were added to a solution of 2-[1-[4-(4-tert-butoxyphenyl)butyl]-1H-imidazol-2-yl]ethanol (4.77 g) in ethyl acetate (50 ml) at 0° C., and the mixture was stirred at 0° C. for 1 hr. The reaction mixture was combined with water and extracted with ethyl acetate. The extract was washed with saturated brine and dried over anhydrous magnesium sulfate. The solvent was evaporated under reduced pressure to give crude 2-[1-[4-(4-tert-butoxyphenyl)butyl]-1H-imidazol-2-yl]ethyl methanesulfonate. Sodium thiomethoxide (2.25 g) was added to a solution of the product in DMF (35 ml), and the mixture was stirred at room temperature for 2.5 hr. The reaction mixture was combined with water and extracted with ethyl acetate. The extract was successively washed with water and saturated brine and dried over anhydrous magnesium sulfate. The solvent was evaporated under reduced pressure, and the residue was purified by silica gel column chromatography (eluent; hexane:ethyl acetate=1:1 to 1:3) to give the titled compound (4.22 g) as a pale yellow oil.

¹H-NMR (CDCl₃) δ: 1.33 (9H, s), 1.52–1.84 (4H, m), 2.11 (3H, s), 2.59 (2H, t, J=7.4 Hz), 2.89–2.96 (4H, m), 3.86 (2H, t, J=7.0 Hz), 6.79 (1H, d, J=1.2 Hz), 6.88–6.95 (3H, m), 7.01–7.05 (2H, m). IR (KBr): 1507, 1366, 1235, 1163, 870 cm⁻¹.

(iv) Production of 4-[4-[2-[2-(methylsulfanyl)ethyl]-1H-imidazol-1-yl]butyl]phenol tert-Butyl 4-[4-[2-[2-(methylsulfanyl)ethyl]-1H-imidazol-1-yl]butyl]phenyl ether (2.11 g) was dissolved in 4N hydrochloric acid (6 ml), and the mixture was stirred at 50° C. for 1 hr. The reaction mixture was neutralized with 30% aqueous sodium hydroxide solution to give crystals, which were collected by filtration and washed with diethyl ether to give the titled compound (1.12 g) as a colorless crystal powder.

¹H-NMR (CDCl₃) δ: 1.56–1.63 (2H, m), 1.70–1.79 (2H, m), 2.03 (3H, s), 2.55 (2H, t, J=7.5 Hz), 2.82–2.94 (4H, m), 3.87 (2H, t, J=7.2 Hz), 6.76–6.80 (3H, m), 6.94–6.98 (3H, m). IR (KBr): 1514, 1489, 1456, 1273, 1250 cm⁻¹.

Reference Example 7

Production of 4-[4-[2-[(methylsulfonyl)methyl]-1H-imidazol-1-yl]butyl]phenol

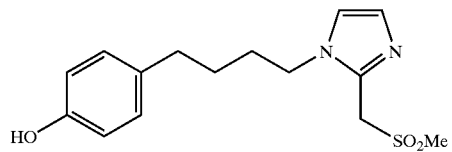

(i) Production of [1-[4-(4-tert-butoxyphenyl)butyl]-1H-imidazol-2-yl]methanol

A suspension of 1-tert-butoxy-4-(4-iodobutyl)benzene (10.0 g), 2-formyl-1H-imidazole (3.47 g) and potassium carbonate (4.16 g) in DMF (100 ml) was stirred at 70° C. for 17 hr. The reaction mixture was combined with water and extracted with ethyl acetate. The extract was successively washed with water (3 times) and saturated brine, dried over anhydrous magnesium sulfate. The solvent was evaporated under reduced pressure to give crude 1-[4-(4-tert-butoxyphenyl)butyl]-1H-imidazole-2-carbaldehyde as a pale brown oil. Sodium borohydride (1.25 g) was added to a solution of the compound in methanol (200 ml) at 0° C., and the mixture was stirred at 0° C. for 1 hr. The reaction mixture was combined with water, concentrated and extracted with ethyl acetate. The extract was washed with saturated brine and dried over anhydrous magnesium sulfate. The solvent was evaporated under reduced pressure, and the residue was purified by silica gel column chromatography (Chromatorex, 100–200 mesh, Fuji silicia chemical) (eluent; hexane:ethyl acetate=1:3 to ethyl acetate) to give the titled compound (8.29 g) as a colorless amorphous form.

¹H-NMR (CDCl₃) δ: 1.32 (9H, s), 1.58–1.86 (4H, m), 2.60 (2H, t, J=7.2 Hz), 3.99 (2H, t, J=7.4 Hz), 4.62 (2H, s), 6.80–6.93 (4H, m), 7.03 (2H, d, J=8.4 Hz). IR (KBr): 1505, 1366, 1235, 1163, 897 cm⁻¹.

(ii) Production of 4-[4-[2-[(methylthio)methyl]-1H-imidazol-1-yl]butyl]phenol

Dimethyl disulfide (8.94 ml) and tributylphosphine (24.7 ml) were added to a solution of [1-[4-(4-tert-butoxyphenyl)butyl]-1H-imidazol-2-yl]methanol (10.0 g) in pyridine (13.4 ml) at room temperature, and the mixture was stirred at room temperature for 17 hr. The reaction mixture was diluted with ethyl acetate, successively washed with 1N aqueous sodium hydroxide solution (3 times) and saturated brine and dried over anhydrous magnesium sulfate. The solvent was evaporated under reduced pressure to give crude 1-[4-(4-tert-butoxyphenyl)butyl]-2-[(methylthio)methyl]-1H-imidazole. 4N Hydrochloric acid (33 ml) was added to the product, and the mixture was stirred at 50° C. for 2 hr. After cooling, the reaction mixture was combined with water and ethyl acetate and separated. The water layer was adjusted to pH 6 by adding 30% aqueous sodium hydroxide solution to salt out and extracted with ethyl acetate. The extract was washed with saturated brine and dried over anhydrous magnesium sulfate. The solvent was evaporated under reduced pressure, and the residue was washed with diisopropyl ether to give the titled compound (7.31 g) as a colorless crystal powder.

¹H-NMR (CDCl₃) δ: 1.58–1.84 (4H, m), 2.02 (3H, s), 2.57 (2H, t, J=7.2 Hz), 3.71 (2H, s), 3.94 (2H, t, J=7.0 Hz), 6.75–6.79 (2H, m), 6.86 (1H, d, J=1.0 Hz), 6.94 (1H, d, J=1.0 Hz), 6.97–7.01 (2H, m). IR (KBr): 2936, 1516, 1489, 1445, 1250 cm⁻¹.

(iii) Production of 4-[4-[2-[(methylsulfonyl)methyl]-1H-imidazol-1-yl]butyl]phenol Oxone (Trade mark; potassium peroxymonosulfate: 28.8 g) was added to a suspension of 4-[4-[2-[(methylthio)methyl]-1H-imidazol-1-yl]butyl]phenol (8.64 g) in methanol-water (2:1) (150 ml) at 0° C. and the mixture was stirred at room temperature for 3.5 hr. The reaction mixture was adjusted to pH 6 by addition of 4N aqueous sodium hydroxide solution to precipitate crystals, which were collected by filtration. The crystals were dissolved in ethyl acetate-methanol (1:4), and the insoluble was filtered off. The filtrated was concentrated and recrystallized from ethyl acetate-methanol-hexane to give the titled compound (6.53 g) as colorless needle crystals.

¹H-NMR (CDCl₃+CD₃OD) δ: 1.54–1.86 (4H, m), 2.57 (2H, t, J=7.0 Hz), 2.95 (3H, s), 4.02 (2H, t, J=6.8 Hz), 4.37 (2H, s), 6.72–6.79 (2H, m), 6.95–7.04 (4H, m). IR (KBr): 1464, 1310, 1250, 1173, 1138 cm⁻¹.

Reference Example 8

Production of 2-[(E)-2-(4-chloro-3-fluorophenyl) ethenyl]-4-(chloromethyl)-1,3-oxazole

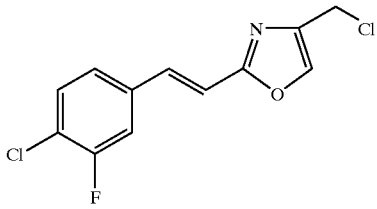

Using (E)-3-(4-chloro-3-fluorophenyl)-2-propenamide (8.67 g) and 1,3-dichloroacetone (11.0 g), the same reaction as Reference Example 1-(ii) was carried out to yield the titled compound (4.95 g) as colorless flaky crystals.

$^1$H-NMR (CDCl$_3$+CD$_3$OD) δ: 4.54 (2H, d, J=0.8 Hz), 6.88 (1H, d, J=16.4 Hz), 7.21–7.49 (4H, m), 7.65 (1H, s). IR (KBr): 1576, 1489, 964, 754, 710 cm$^{-1}$.

Example 1

Production of 2-[1-[4-[4-[[2-[(E)-2-[4-(trifluoromethyl)phenyl]ethenyl]-1,3-oxazol-4-yl] methoxy]phenyl]butyl]-1H-imidazol-2-yl]ethyl isopropylcarbamate

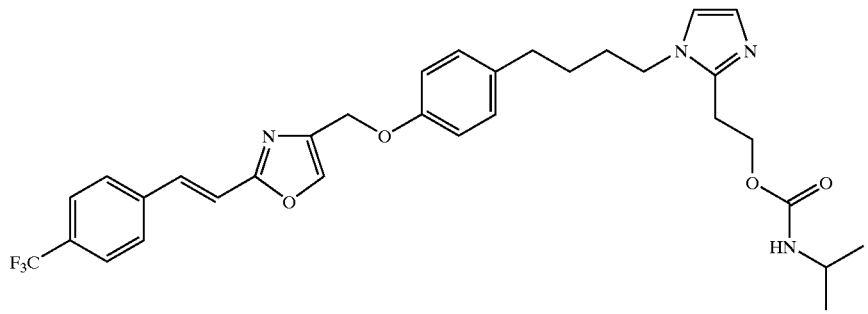

65% Sodium hydride (21.6 mg) was added to a solution of 2-[1-[4-[4-[[2-[(E)-2-[4-(trifluoromethyl)phenyl] ethenyl]-1,3-oxazol-4-yl]methoxy]phenyl]butyl]-1H-imidazol-2-yl]-1-ethanol (300 mg) in dichloromethane (3 ml) at 0° C., and the mixture was stirred at room temperature for 30 min. Isopropyl isocyanate (0.288 ml) was added to the mixture at 0° C., and the mixture was stirred at room temperature for 5 hr. The reaction mixture was combined with water and extracted with ethyl acetate. The extract was successively washed with 1N aqueous sodium hydroxide solution and saturated brine and dried over anhydrous magnesium sulfate. The solvent was evaporated under reduced pressure and recrystallized from ethyl acetate-hexane to give the titled compound (315 mg) as a colorless crystal powder.

$^1$H-NMR (CDCl$_3$) δ: 1.12–1.16 (6H, m), 1.61–1.66 (2H, m) 1.71–1.80 (2H, m), 2.59 (2H, t, J=7.5 Hz), 2.97 (2H, t, J=7.2 Hz), 3.81–3.89 (3H, m), 4.41 (2H, t, J=7.2 Hz), 4.53 (1H, br s), 5.02 (2H, d, J=0.6 Hz), 6.81 (1H, d, J=1.2 Hz), 6.91–7.09 (6H, m), 7.53–7.69 (6H, m). IR (KBr): 1711, 1512, 1325, 1246, 1069 cm$^{-1}$.

Example 2

Production of 2-[1-[4-[4-[[2-[(E)-2-[4-(trifluoromethyl)phenyl]ethenyl]-1,3-oxazol-4-yl] methoxy]phenyl]butyl]-1H-imidazol-2-yl]ethyl methylcarbamate

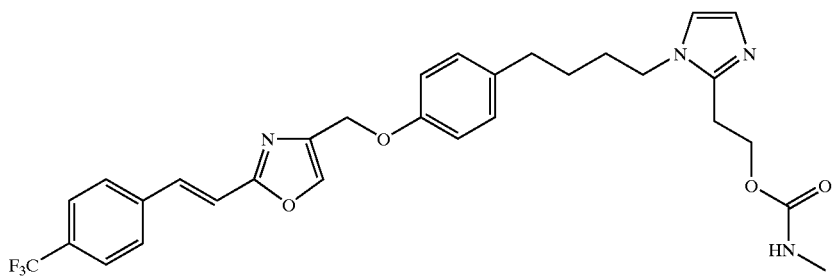

1,1'-Carbonyldiimidazole (143 mg) was added to a solution of 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]-1-ethanol (300 mg) in THF (3 ml) at 0° C., and the mixture was stirred at the same temperature for 3 hr. A solution (2.0 M; 1.47 ml) of methylamine in THF was added to the reaction mixture at 0° C., and the mixture was stirred at the same temperature for 3 hr and at room temperature for 30 min. The reaction mixture was combined with water and extracted with ethyl acetate. The extract was washed with saturated brine and dried over anhydrous magnesium sulfate. The solvent was concentrated under reduced pressure and recrystallized from diethyl ether-acetone-hexane to give the titled compound (310 mg) as a colorless crystal powder.

$^1$H-NMR (CDCl$_3$) δ: 1.61–1.75 (4H, m), 2.59 (2H, t, J=7.0 Hz), 2.77 (2H, t, J=5.2 Hz), 2.97 (3H, t, J=6.8 Hz), 3.87 (2H, t, J=7.2 Hz), 4.43 (2H, t, J=6.8 Hz), 4.62 (1H, br, s), 5.02 (2H, d, J=0.8 Hz), 6.81 (1H, d, J=1.0 Hz), 6.90–7.12 (6H, m), 7.26–7.69 (6H, m). IR (KBr): 1715, 1510, 1325, 1125, 1067 cm$^{-1}$.

Example 3

Production of 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethyl 1-pyrroridinecarboxylate

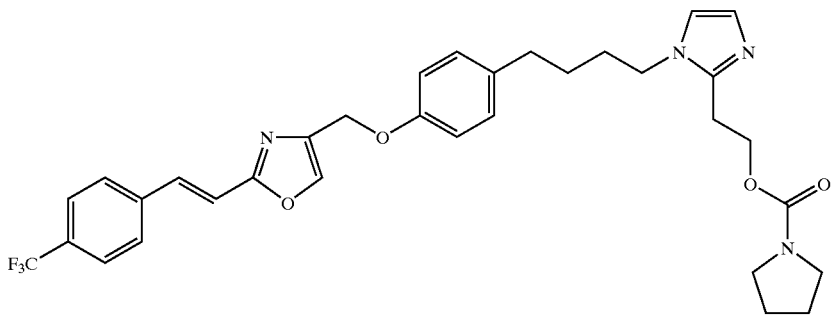

Using 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]-1-ethanol (300 mg), 1,1'-carbonyldiimidazole (143 mg) and pyrrolidine (0.147 ml), the same reaction as Example 2 was carried out to yield the titled compound (258 mg) as a colorless crystal powder.

$^1$H-NMR (CDCl$_3$) δ: 1.56–1.66 (2H, m), 1.71–1.79 (2H, m), 1.82–1.84 (4H, m), 2.58 (2H, t, J=7.2 Hz), 3.02 (2H, t, J=7.5 Hz), 3.29 (2H, t, J=6.6 Hz), 3.38 (2H, t, J=6.6 Hz), 3.90 (2H, t, J=7.5 Hz), 4.41 (2H, t, J=7.2 Hz), 5.02 (2H, d, J=1.2 Hz), 6.81 (1H, d, J=1.2 Hz), 6.89–7.11 (6H, m), 7.53–7.69 (6H, m). IR (KBr): 1698, 1510, 1125, 1111, 1067 cm$^{-1}$.

Example 4

Production of ethyl 3-[1-[4-[4-[[2-[(E)-2-[4-(trifluoromethyl)phenyl]ethenyl]-1,3-oxazol-4-yl]methoxy]phenyl]butyl]-1H-imidazol-2-yl]propionate

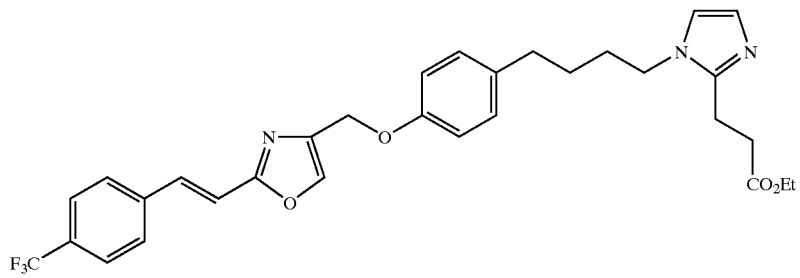

(i) Production of 4-[[4-(4-iodobutyl)phenoxy] methyl]-2-[(E)-2-[4-(trifluoromethyl)phenyl] ethenyl]-1,3-oxazole A suspension of 4-chloromethyl-2-[(E)-2-[4-(trifluoromethyl)phenyl]ethenyl]-1,3-oxazole (13.4 g), 4-(4-chlorobutyl)phenol (8.63 g) and potassium carbonate (6.46 g) in DMF (200 ml) was stirred at 60° C. for 24 hr. The reaction mixture was combined with water to give crystals, which were collected by filtration and washed with methanol-water (2:1) to give crude 4-[[4-(4-chlorobutyl) phenoxy]methyl]-2-[(E)-2-[4-(trifluoromethyl)phenyl] ethenyl]-1,3-oxazole (19.5 g) as colorless powders. A suspension of this product (18.5 g) and sodium iodide (31.8 g) in acetonitrile (240 ml) was refluxed for 22 hr. The reaction mixture was concentrated, diluted with ethyl acetate, successively washed with water, hypo-water and saturated brine and dried over anhydrous magnesium sulfate. The solvent was evaporated under reduced pressure, and the residue was washed with hexane to give the titled compound (12.3 g) as colorless needle crystals.

$^1$H-NMR (CDCl$_3$) δ: 1.66–1.93 (4H, m), 2.59 (2H, t, J=7.6 Hz), 3.20 (2H, t, J=7.0 Hz), 5.03 (2H, t, J=1.0 Hz), 6.97–7.13 (5H, m), 7.52–7.69 (6H, m). IR (KBr): 1512, 1323, 1167, 1128, 1067 cm$^{-1}$.

(ii) Production of ethyl 3-[1-[4-[4-[[2-[(E)-2-[4-(trifluoromethyl)phenyl]ethenyl]-1,3-oxazol-4-yl] methoxy]phenyl]butyl]-1H-imidazol-2-yl]propionate A suspension of 4-[[4-(4-iodobutyl)phenoxy]methyl]-2-[(E)-2-[4-(trifluoromethyl)phenyl]ethenyl]-1,3-oxazole (6.00 g), ethyl 3-(1H-imidazol-2-yl)propionate (3.83 g) and potassium carbonate (1.58 g) in DMF (100 ml) was stirred at 70° C. for 23 hr. The reaction mixture was combined with water and extracted with ethyl acetate. The extract was successively washed with water and saturated brine and dried over magnesium sulfate. The solvent was evaporated under reduced pressure, and the residue was purified by silica gel column chromatography (eluent; ethyl acetate) and washed with diethyl ether-hexane to give the titled compound (3.69 g) as a colorless amorphous form.

$^1$H-NMR (CDCl$_3$) δ: 1.25 (3H, t, J=7.2 Hz), 1.59–1.79 (4H, m), 2.59 (2H, t, J=7.0 Hz), 2.88–2.91 (4H, m), 3.87 (2H, t, J=7.0 Hz), 4.14 (2H, q, J=7.2 Hz), 5.02 (2H, d, J=0.8 Hz), 6.79 (1H, d, J=1.4 Hz), 6.90–7.06 (6H, m), 7.10 (1H, s), 7.52–7.69 (5H, m). IR (KBr): 1732, 1510, 1325, 1167, 1123, 1067 cm$^{-1}$.

Example 5

Production of N,N-dimethyl-3-[1-[4-[4-[[2-[(E)-2-[4-(trifluoromethyl)phenyl]ethenyl]-1,3-oxazol-4-yl] methoxy]phenyl]butyl]-1H-imidazol-2-yl] propanamide

(i) Production of 3-[1-[4-[4-[[2-[(E)-2-[4-(trifluoromethyl)phenyl]ethenyl]-1,3-oxazol-4-yl] methoxy]phenyl]butyl]-1H-imidazol-2-yl]propionic acid 1N Sodium hydroxide (13 ml) was added to a solution of ethyl 3-[1-[4-[4-[[2-[(E)-2-[4-(trifluoromethyl)phenyl] ethenyl]-1,3-oxazol-4-yl]methoxy]phenyl]butyl]-1H-imidazol-2-yl]propionate (3.69 g) in methanol (50 ml), and the mixture was refluxed for 5.5 hr. The reaction mixture was neutralized with 1N hydrochloric acid and concentrated. The precipitated crystals were filtered, washed with water and recrystallized from ethyl acetate-methanol-hexane to give the titled compound (2.24 g) as a colorless crystal powder.

$^1$H-NMR (DMSO-d$_6$) δ: 1.51–1.67 (4H, m), 2.54 (2H, t, J=7.0 Hz), 2.66 (2H, t, J=6.2 Hz), 2.80 (2H, t, J=6.2 Hz), 3.90 (2H, t, J=6.6 Hz), 4.99 (2H, s), 6.76 (1H, s), 6.94 (2H, d, J=8.4 Hz), 7.04–7.14 (3H, m), 7.34 (1H, d, J=16.6 Hz), 7.62 (1H, d, J=16.6 Hz), 7.76 (2H, d, J=8.0 Hz), 7.96 (2H, d, J=8.0 Hz), 8.24 (1H, s). IR (KBr): 1512, 1325, 1244, 1165, 1130, 1069 cm$^{-1}$.

(ii) Production of N,N-dimethyl-3-[1-[4-[4-[[2-[(E)-2-[4-(trifluoromethyl)phenyl]ethenyl]-1,3-oxazol-4-yl]methoxy]phenyl]butyl]-1H-imidazol-2-yl] propanamide A solution (2M; 0.557 ml) of N,N-dimethylamine in THF and diethyl cyanophosphate (67.6 µl) were added to a solution of 3-[1-[4-[4-[[2-[(E)-2-[4-(trifluoromethyl) phenyl]ethenyl]-1,3-oxazol-4-yl]methoxy]phenyl]butyl]-1H-imidazol-2-yl]propionic acid (200 mg) in DMF (3 ml) at 0° C., and the mixture was stirred for 15 min. Triethylamine (77.6 µl) was added to the mixture at 0° C., and the mixture was stirred at room temperature for 16 hr. The reaction mixture was combined with water and extracted with ethyl acetate. The extract was successively washed with water and saturated brine and dried over magnesium sulfate. The solvent was evaporated under reduced pressure, and the residue was purified by silica gel column chromatography (eluent; dichloromethane to dichloromethane:methanol= 20:1) and recrystallized from diethyl ether-ethyl acetate-hexane to give the titled compound (146 mg) as a colorless crystal powder.

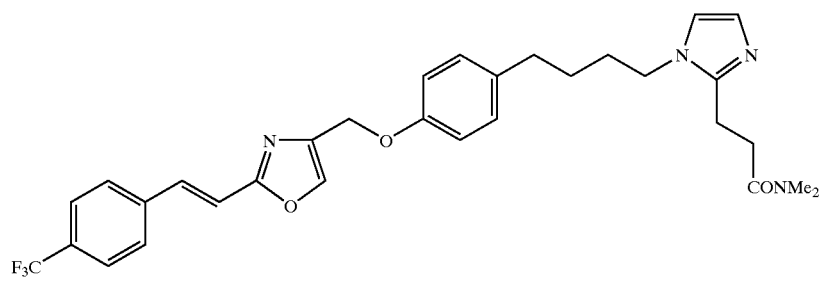

¹H-NMR (CDCl₃) δ: 1.68–1.72 (4H, m), 2.58 (2H, t, J=6.6 Hz), 2.93–2.95 (7H, m), 3.04 (3H, s), 3.91 (2H, t, J=7.0 Hz), 5.02 (2H, s), 6.79 (1H, d, J=1.8 Hz), 6.89–7.10 (6H, m), 7.52–7.69 (6H, m). IR (KBr): 1647, 1510, 1325, 1123, 1067 cm⁻¹.

Example 6

Production of 1-{3-[1-(4-{4-[(2-{(E)-2-[4-(trifluoromethyl)phenyl]ethenyl}-1,3-oxazol-4-yl)methoxy]phenyl}butyl)-1H-imidazol-2-yl]propanoyl}pyrrolidine

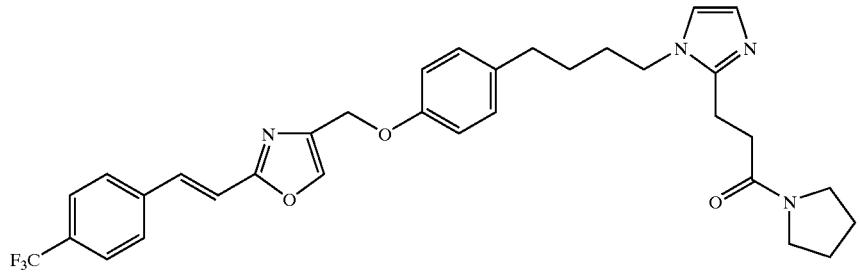

Using 3-[1-[4-[4-[(2-[(E)-2-[4-(trifluoromethyl)phenyl]ethenyl]-1,3-oxazol-4-yl)methoxy]phenyl]butyl]-1H-imidazol-2-yl]propionic acid (200 mg), pyrrolidine (0.174 ml), diethyl cyanophosphate (0.303 ml) and triethylamine (0.310 ml), the same reaction as Example 5-(ii) was carried out to yield the titled compound (86 mg).

¹H-NMR (CDCl₃) δ: 1.71–1.97 (8H, m), 2.58 (2H, t, J=7.4 Hz), 2.81–3.02 (4H, m), 3.42–3.49 (4H, m), 3.91 (2H, t, J=7.0 Hz), 5.02 (2H, s), 6.79 (1H, d, J=1.0 Hz), 6.89–7.10 (6H, m), 7.52–7.69 (6H, m). IR (KBr): 1638, 1510, 1325, 1123, 1067 cm⁻¹.

Example 7

Production of 4-{3-[1-(4-{4-[(2-{(E)-2-[4-(trifluoromethyl)phenyl]ethenyl}-1,3-oxazol-4-yl)methoxy]phenyl}butyl)-1H-imidazol-2-yl]propanoyl}morpholine

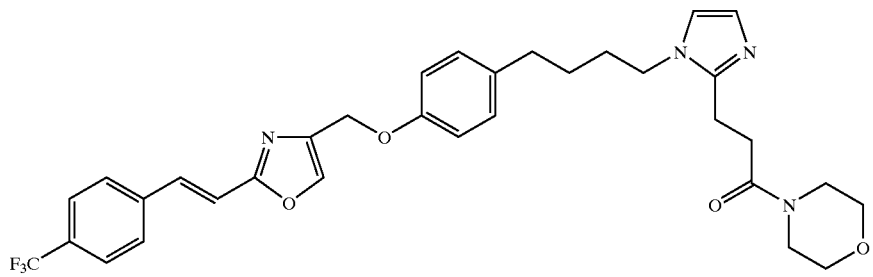

Using 3-[1-[4-[4-[(2-[(E)-2-[4-(trifluoromethyl)phenyl]ethenyl]-1,3-oxazol-4-yl)methoxy]phenyl]butyl]-1H-imidazol-2-yl]propionic acid (200 mg), morpholine (97.1 μl), diethyl cyanophosphate (84.5 μl) and triethylamine (77.6 μl), the same reaction as Example 5-(ii) was carried out to yield the titled compound (217 mg).

¹H-NMR (CDCl₃) δ: 1.58–1.66 (2H, m), 1.70–1.80 (2H, m), 2.58 (2H, t, J=7.2 Hz), 2.88–3.00 (4H, m), 3.52–3.56 (2H, m), 3.60–3.67 (6H, m), 3.90 (2H, t, J=6.9 Hz), 5.02 (2H, s), 6.80 (1H, d, J=2.7 Hz), 6.90–7.12 (6H, m), 7.53–7.69 (6H, m). IR (KBr): 1644, 1510, 1325, 1242, 1115, 1067 cm⁻¹.

Example 8

Production of N-methyl-3-[1-[4-[4-[[2-[(E)-2-[4-(trifluoromethyl)phenyl]ethenyl]-1,3-oxazol-4-yl]methoxy]phenyl]butyl]-1H-imidazol-2-yl]propanamide

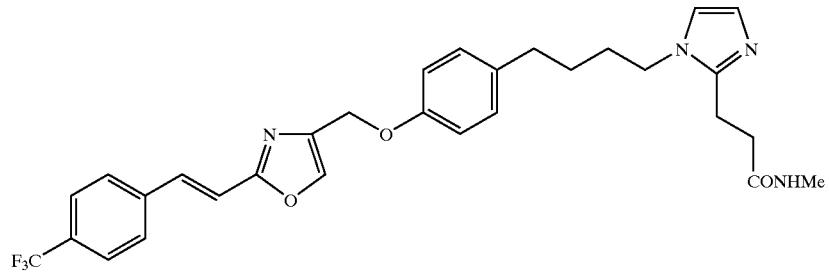

A mixture of ethyl 3-[1-[4-[4-[[2-[(E)-2-[4-(trifluoromethyl)phenyl]ethenyl]-1,3-oxazol-4-yl]methoxy]phenyl]butyl]-1H-imidazol-2-yl]propionate (180 mg) and a solution (3 ml) of 30% methylamine in ethanol in sealed tube was heated at 120° C. for 12 hr. The reaction mixture was concentrated, and the residue was purified by silica gel column chromatography (eluent; dichloromethane to dichloromethane:methanol=30:1) and recrystallized from ethyl acetate-hexane to give the titled compound (43 mg) as a colorless crystal powder.

$^1$H-NMR (CDCl$_3$) δ: 1.55–1.65 (2H, m), 1.69–1.78 (2H, m), 2.59 (2H, t, J=7.2 Hz), 271–2.77 (5H, m), 2.93 (2H, t, J=6.9 Hz), 3.85 (2H, t. J=7.2 Hz), 5.02 (2H, s), 6.62 (1H, br, s), 6.80 (1H, s), 6.91–7.09 (6H, m), 7.53–7.70 (6H, m). IR (KBr): 1647, 1512, 1321, 1174, 1165, 1067 cm$^{-1}$.

Example 9

Production of N-[2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethyl]acetamide

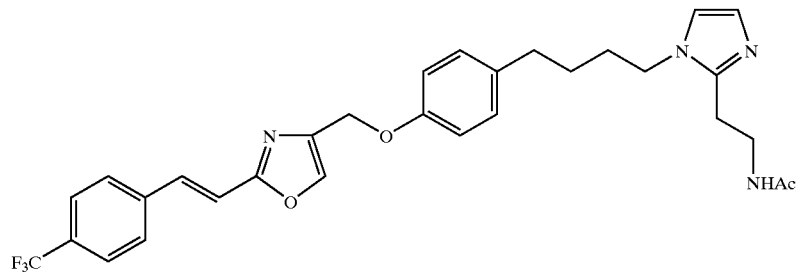

(i) Production of 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethylamine Diethyl azodicarboxylate (1.86 ml) was added to a solution of 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]-1-ethanol (2.00 g), phthalimide (605 mg) and triphenylphosphine (1.08 g) in THF (30 ml) at room temperature, and the mixture was stirred for 24 hr. The reaction mixture was diluted with ethyl acetate, successively washed with 1N aqueous sodium hydroxide solution and saturated brine and dried over anhydrous magnesium sulfate. The solvent was evaporated under reduced pressure to give crude 2-[2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethyl]-1H-isoindole-1,3(2H)-dione (4.31 g) as pale yellow crystals. 2-Aminoethannol (4.31 ml) was added to a solution of the product (3.94 g) in ethanol (70 ml), and the mixture was refluxed for 75 min. The reaction mixture was concentrated, diluted with ethyl acetate, successively washed with water and saturated brine and dried over anhydrous sodium sulfate. The solvent was evaporated under reduced pressure, and the residue was purified by silica gel column chromatography (Chromatorex, 100–200 mesh, Fuji silicia chemical) (eluent; dichloromethane to dichloromethane:methanol=200:1 to 40:1) to give the titled compound (1.34 g) as a colorless amorphous form.

$^1$H-NMR (CDCl$_3$) δ: 1.56–1.66 (2H, m), 1.69–1.74 (2H, m), 2.59 (2H, t, J=7.2 Hz), 2.15 (2H, t, J=6.6 Hz), 2.76 (2H, t. J=6.6 Hz), 3.84 (2H, d, J=7.2 Hz), 5.02 (2H, d, J=0.9 Hz), 6.81 (1H, s), 6.91–7.06 (6H, m), 7.53–7.69 (6H, m). IR (KBr): 1508, 1325, 1173, 1138, 1067 cm$^{-1}$.

(ii) Production of N-[2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethyl]acetamide Triethylamine (137 μl) and acetic anhydride (74.0 μl) were added to a solution of 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethylamine (200 mg) in THF at 0° C., and the mixture was stirred at 0° C. for 1.5 hr. The reaction mixture was combined with water and extracted with ethyl acetate. The extract was washed with saturated brine and dried over anhydrous magnesium sulfate. The solvent was evaporated under reduced pressure, and the residue was purified by silica gel column chromatography (eluent; dichloromethane to dichloromethane:methanol=20:1) and recrystallized from ethyl acetate-hexane to give the titled compound (123 mg) as colorless needle crystals.

¹H-NMR (CDCl₃) δ: 1.55–1.65 (2H, m), 1.69–1.78 (2H, m). 1.95 (3H, s), 2.59 (2H, t, J=7.5 Hz), 2.78 (2H, t, J=6.0 Hz), 3.70 (2H, dt, J=6.0, 6.0 Hz), 3.82 (2H, t, J=6.9 Hz), 5.02 (2H, d, J=0.6 Hz), 6.83–7.09 (8H, m), 7.53–7.70 (6H, m). IR (KBr): 1665, 1510, 1325, 1123, 1067 cm⁻¹.

Example 10

Production of N-ethyl-N'-[2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethyl]urea

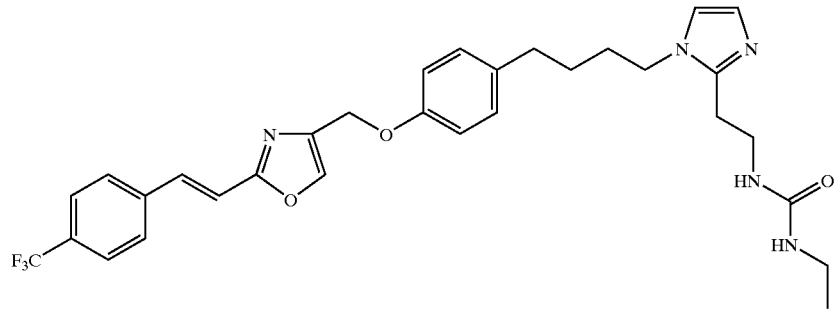

Ethyl isocyanate (62.0 µl) was added to a solution of 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethylamine (200 mg) in pyridine (2 ml) at 0° C., and the mixture was stirred at 0° C. for 1.5 hr and at room temperature for 22 hr. The reaction mixture was combined with water to give crystals, which were collected by filtration, washed with diethyl ether and recrystallized from ethyl acetate-methanol-hexane to give the titled compound (161 mg) as colorless needle crystals.

¹H-NMR (CDCl₃) δ: 1.10 (3H, t, J=7.2 Hz), 1.59–1.78 (4H, m), 2.58 (2H, t, J=6.6 Hz), 2.78 (2H, t, J=5.8 Hz), 3.10–3.23 (2H, m), 3.64 (2H, dt, J=5.8, 5.8 Hz), 3.82 (2H, t, J=7.4 Hz), 4.50 (1H, br s), 5.02 (2H, d, J=0.8 Hz), 5.52 (1H, br s), 6.81 (1H, d, J=1.2 Hz), 6.90–7.10 (6H, m), 7.52–7.69 (6H, m). IR (KBr): 1614, 1576, 1512, 1325, 1069 cm⁻¹.

Example 11

Production of 2-[(E)-2-(4-fluorophenyl)ethenyl]-4-[[4-[4-[2-[2-(methylsulfonyl)ethyl]-1H-imidazol-1-yl]butyl]phenoxy]methyl]-1,3-oxazole (i) Production of 2-[(E)-2-(4-fluorophenyl)ethenyl]-4-[[4-[4-[2-[2-(methylsulfanyl)ethyl]-1H-imidazol-1-yl]butyl]phenoxy]methyl]-1,3-oxazole 65% Sodium hydride (63.1 mg) was added to a solution of 4-[[4-[4-[2-[2-(methylsulfanyl)ethyl]-1H-imidazol-1-yl]butyl]phenol (300 mg) in DMF (5 ml) at 0° C., and the mixture was stirred at room temperature for 30 min. 4-Chloromethyl-2-[(E) -2-(4-fluorophenyl)ethenyl]-1,3-oxazole (269 mg) was added to the mixture, and the mixture was stirred at room temperature for 1 hr. The reaction mixture was combined with water and extracted with ethyl acetate. The extract was successively washed with water and saturated brine and dried over anhydrous magnesium sulfate. The solvent was evaporated under reduced pressure, and the residue was purified by silica gel column chromatography (eluent; hexane:ethyl acetate=2:3 to ethyl acetate) to give the titled compound (374 mg) as a colorless amorphous form.

¹H-NMR (CDCl₃) δ: 1.62–1.80 (4H, m), 2.11 (3H, s), 2.59 (2H, t, J=7.0 Hz), 2.92 (4H, s), 3.86 (2H, t, J=6.8 Hz), 5.01 (2H, d, J=1.2 Hz), 6.79–7.13 (9H, m), 7.46–7.65 (4H, m). IR (KBr): 1601, 1532, 1510, 1233, 826 cm⁻¹.

(ii) Production of 2-[(E)-2-(4-fluorophenyl)ethenyl]-4-[[4-[4-[2-[2-(methylsulfonyl)ethyl]-1H-imidazol-1-yl]butyl]phenoxy]methyl]-1,3-oxazole A solution of 70% m-chloroperbenzoic acid (188 mg) in THF (2.5 ml) was added to a solution of 2-[(E)-2-(4-fluorophenyl)ethenyl]-4-[[4-[4-[2-[2-(methylsulfanyl) ethyl]-1H-imidazol-1-yl]butyl]phenoxy]methyl]-1,3-oxazole (150 mg) in THF (2 ml) at 0° C., and the mixture was stirred at 0° C. for 10 min. The reaction mixture was combined with saturated aqueous sodium hydrogen carbonate solution and extracted with ethyl acetate. The extract was successively washed with saturated aqueous sodium hydrogen carbonate solution and saturated brine and dried over anhydrous magnesium sulfate. The solvent was evaporated under reduced pressure, and the residue was purified by

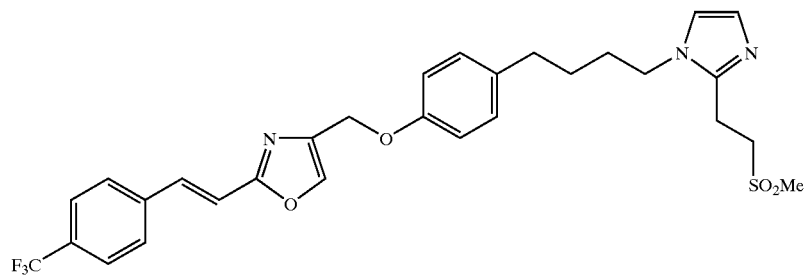

silica gel column chromatography (eluent; ethyl acetate to ethyl acetate:methanol=96:4) to give the titled compound (47 mg) as a colorless amorphous form.

$^1$H-NMR (CDCl$_3$) δ: 1.62–1.69 (4H, m), 2.60 (2H, t, J=6.6 Hz), 2.84 (3H, s), 3.15 (2H, t, J=7.4 Hz), 3.63 (2H, t, J=7.4 Hz), 3.88 (2H, t, J=7.0 Hz), 5.01 (2H, s), 6.82–7.13 (9H, m), 7.47–7.66 (4H, m). IR (KBr): 1508, 1306, 1233, 1128, 826 cm$^{-1}$.

Example 12

Production of 2-[(E)-2-(2,4-difluorophenyl)ethenyl]-4-[[4-[4-[2-[2-(methylsulfonyl)ethyl]-1H-imidazol-1-yl]butyl]phenoxy]methyl]-1,3-oxazole

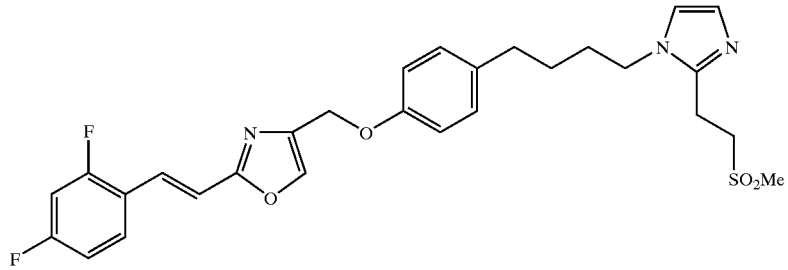

(i) Production of 2-[(E)-2-(2,4-difluorophenyl)ethenyl]-4-[[4-[4-[2-[2-(methylsulfanyl)ethyl]-1H-imidazol-1-yl]butyl]phenoxy]methyl]-1,3-oxazole Using 4-[4-[4-[2-[2-(methylsulfanyl)ethyl]-1H-imidazol-1-yl]butyl]phenol (500 mg), 65% sodium hydride (69.8 mg) and 4-chloromethyl-2-[(E)-2-(2,4-difluorophenyl)ethenyl]-1,3-oxazole (483 mg), the same reaction as Example 11-(i) was carried out to yield the titled compound (812 mg) as a colorless amorphous form.

$^1$H-NMR(CDCl$_3$) δ: 1.61–1.72 (4H, m), 2.11 (3H, s), 2.59 (2H, t, J=7.4 Hz), 2.82–3.02 (4H, m), 3.86 (2H, t, J=7.4 Hz), 5.02 (2H, s), 6.80–7.10 (9H, m), 7.48–7.67 (3H, m). IR (KBr): 1613, 1510, 1273, 1246, 966 cm$^{-1}$.

(ii) Production of 2-[(E)-2-(2,4-difluorophenyl)ethenyl]-4-[[4-[4-[2-[2-(methylsulfonyl)ethyl]-1H-imidazol-1-yl]butyl]phenoxy]methyl]-1,3-oxazole Using 2-[(E)-2-(2,4-difluorophenyl)ethenyl]-4-[[4-[4-[2-[2-(methylsulfanyl)ethyl]-1H-imidazol-1-yl]butyl]phenoxy]methyl]-1,3-oxazole (300 mg) and 70% m-chloroperbenzoic acid (363 mg), the same reaction as Example 11-(ii) was carried out to yield the titled compound (193 mg) as a colorless crystal powder.

$^1$H-NMR(CDCl$_3$) δ: 1.61–1.83 (4H, m), 2.60 (2H, t, J=7.0 Hz), 2.84 (3H, s), 3.15 (2H, t, J=7.2 Hz), 3.63 (2H, t, J=7.2 Hz), 3.88 (2H, t, J=7.2 Hz), 5.02 (2H, d, J=0.8 Hz), 6.84 (1H, d, J=1.2 Hz), 6.91–7.11 (6H, m), 7.49–7.76 (5H, m). IR (KBr): 1510, 1306, 1275, 1140, 966 cm$^{-1}$.

Example 13

Production of 4-[[4-[4-[2-[(methylsulfonyl)methyl]-1H-imidazol-1-yl]butyl]phenoxy]methyl]-2-[(E)-2-[4-(trifluoromethyl)phenyl]ethenyl]-1,3-oxazole

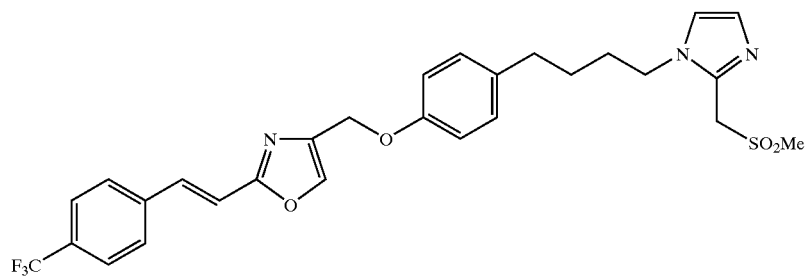

(i) Production of 1-[4-[4-[[2-[(E)-2-[4-(trifluoromethyl)phenyl]ethenyl]-1,3-oxazol-4-yl]methoxy]phenyl]butyl]-1H-imidazole-2-carbaldehyde Using 4-[4-(4-iodobutyl)phenoxy]methyl]-2-[(E)-2-[4-(trifluoromethyl)phenyl]ethenyl]-1,3-oxazole (4.00 g), 2-formyl-1H-imidazole (911 mg) and potassium carbonate (1.05 g), the same reaction as Example 4-(ii) was carried out to yield the titled compound (3.76 g) as a colorless crystal powder.

$^1$H-NMR(CDCl$_3$) δ: 1.57–1.63 (2H, m), 1.78–1.86 (2H, m), 2.59 (2H, t, J=7.0 Hz), 4.41 (2H, t, J=7.4 Hz), 5.02 (2H, t, J=0.8 Hz), 6.89–6.98 (2H, m), 7.06–7.12 (3H, m), 7.26–7.28 (2H, m), 7.52–7.69 (6H, m), 9.81 (1H, d, J=0.6 Hz). IR (KBr): 1676, 1512, 1412, 1325, 1175, 1067 cm$^{-1}$.

(ii) Production of [1-[4-[4-[[2-[(E)-2-[4-(trifluoromethyl)phenyl]ethenyl]-1,3-oxazol-4-yl]methoxy]phenyl]butyl]-1H-imidazol-2-yl]methanol Sodium borohydride (193 mg) was added to a solution of 1-[4-[4-[[2-[(E)-2-[4-(trifluoromethyl)phenyl]ethenyl]-1,3-oxazol-4-yl]methoxy]phenyl]butyl]-1H-imidazole-2-carbaldehyde (2.30 g) in methanol at 0° C., and the mixture was stirred at 0° C. for 1 hr. The reaction mixture was combined with water and concentrated to give crystals, which were washed with water and recrystallized from ethyl acetate-hexane to give the titled compound (2.16 g) as a colorless crystal powder.

$^1$H-NMR(CDCl$_3$) δ: 1.62–1.81 (4H, m), 2.59 (2H, t, J=6.8 Hz), 3.98 (2H, t, J=7.2 Hz), 4.65 (2H, s), 5.02 (2H, s), 6.84 (1H, d, J=1.2 Hz), 6.90–7.10 (6H, m), 7.51–7.69 (6H, m). IR (KBr): 1510, 1323, 1173, 1136, 1067 cm$^{-1}$.

(iii) Production of 4-[[4-[4-[2-[(methylsulfanyl)methyl]-1H-imidazol-1-yl]butyl]phenoxy]methyl]-2-[(E)-2-[4-(trifluoromethyl)phenyl]ethenyl]-1,3-oxazole Pyridine (0.600 ml), dimethyl disulfide (0.217 ml) and tributylphosphine (0.600 ml) were added to a solution of [1-[4-[4-[[2-[(E)-2-[4-(trifluoromethyl)phenyl]ethenyl]-1,3-oxazol-4-yl]methoxy]phenyl]butyl]-1H-imidazol-2-yl]methanol (400 mg) in dichloromethane (8 ml) at room temperature, and the mixture was stirred at room temperature for 6 hr. The reaction mixture was combined with 1N aqueous sodium hydroxide solution and extracted with ethyl acetate. The extract was washed with saturated brine and dried over anhydrous magnesium sulfate. The solvent was evaporated under reduced pressure, and the residue was purified by silica gel column chromatography (eluent; hexane:ethyl acetate=1:1 to ethyl acetate), and recrystallized from ethyl acetate-diethyl ether-hexane to give the titled compound (213 mg) as a colorless crystal powder.

$^1$H-NMR(CDCl$_3$) δ: 1.68–1.86 (4H, m), 2.06 (3H, s), 2.61 (2H, t, J=7.0 Hz), 3.73 (2H, s), 3.94 (2H, t, J=7.0 Hz), 5.02 (2H, d, J=1.0 Hz), 6.85 (1H, d, J=1.4 Hz), 6.90–7.11 (6H, m), 7.52–7.69 (6H, m). IR (KBr): 1508, 1325, 1167, 1123, 1067 cm$^{-1}$.

(iv) Production of 4-[[4-[4-[2-[(methylsulfonyl)methyl]-1H-imidazol-1-yl]butyl]phenoxy]methyl]-2-[(E)-2-[4-(trifluoromethyl)phenyl]ethenyl]-1,3-oxazole Using 4-[[4-[4-[2-[(methylsulfanyl)methyl]-1H-imidazol-1-yl]butyl]phenoxy]methyl]-2-[(E)-2-[4-(trifluoromethyl)phenyl]ethenyl]-1,3-oxazole (110 mg) and 70% m-chloroperbenzoic acid (128 mg), the same reaction as Example 11-(ii) was carried out to yield the titled compound (65 mg) as colorless needle crystals.

$^1$H-NMR(CDCl$_3$) δ: 1.64–1.86 (4H, m), 2.61 (2H, t, J=7.4 Hz), 3.00 (3H, s), 4.03 (2H, t, J=7.4 Hz), 4.36 (2H, s), 5.03 (2H, s), 6.91–7.16 (7H, m), 7.52–7.74 (6H, m). IR (KBr): 1510, 1325, 1306, 1134, 1067 cm$^{-1}$.

Example 14

Production of 2-[(E)-2-(2,6-difluorophenyl)ethenyl]-4-[[4-[4-[2-[2-(methylsulfonyl)ethyl]-1H-imidazol-1-yl]butyl]phenoxy]methyl]-1,3-oxazole

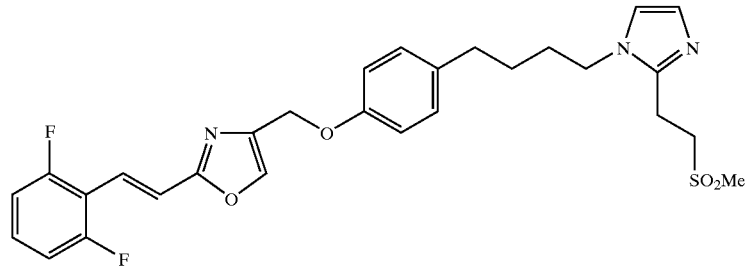

(i) Production of 2-[(E)-2-(2,6-difluorophenyl)ethenyl]-4-[[4-[4-[2-[2-(methylsulfanyl)ethyl]-1H-imidazol-1-yl]butyl]phenoxy]methyl]-1,3-oxazole Using 4-[4-[2-[2-(methylsulfanyl)ethyl]-1H-imidazol-1-yl]butyl]phenol (300 mg), 65% sodium hydride (63.1 mg) and 4-chloromethyl-2-[(E)-2-(2,6-difluorophenyl)ethenyl]-1,3-oxazole (290 mg), the same reaction as Example 11-(i) was carried out to yield the titled compound (381 mg) as a colorless amorphous form.

$^1$H-NMR (CDCl$_3$) δ: 1.57–1.83 (4H, m), 2.11 (3H, s), 2.59 (2H, t, J=7.0 Hz), 2.92 (4H, s), 3.86 (2H, t, J=6.8 Hz), 5.03 (2H, d, J=0.6 Hz), 6.98 (1H, d, J=1.0 Hz), 6.90–7.10 (5H, m), 7.19–7.33 (4H, m), 7.61 (1H, d, J=16.8 Hz), 7.68 (1H, s). IR (KBr): 1510, 1458, 1240, 1001, 785 cm$^{-1}$.

(ii) Production of 2-[(E)-2-(2,6-difluorophenyl)ethenyl]-4-[[4-[4-[2-[2-(methylsulfonyl)ethyl]-1H-imidazol-1-yl]butyl]phenoxy]methyl]-1,3-oxazole Using 2-[(E)-2-(2,6-difluorophenyl)ethenyl]-4-[[4-[4-[2-[2-(methylsulfanyl)ethyl]-1H-imidazol-1-yl]butyl]phenoxy]methyl]-1,3-oxazole (150 mg) and 70% m-chloroperbenzoic acid (181 mg), the same reaction as Example 11-(ii) was carried out to yield the titled compound (63 mg) as a colorless crystal powder.

$^1$H-NMR(CDCl$_3$) δ: 1.64–1.75 (4H, m), 2.60 (2H, t, J=6.6 Hz), 2.84 (3H, s), 3.15 (2H, t, J=8.0 Hz), 3.63 (2H, t, J=8.0 Hz), 3.88 (2H, t, J=7.2 Hz), 5.02 (2H, s), 6.84 (1H, d, J=1.2 Hz), 6.94–7.33 (9H, m), 7.61 (1H, d, J=16.4 Hz), 7.69 (1H, s). IR (KBr): 1510, 1458, 1306, 1240, 1001 cm$^{-1}$.

Example 15

Production of 4-[[4-[4-[2-[2-(methylsulfinyl)ethyl]-1H-imidazol-1-yl]butyl]phenoxy]methyl]-2-[(E)-2-[4-(trifluoromethyl)phenyl]ethenyl]-1,3-oxazole

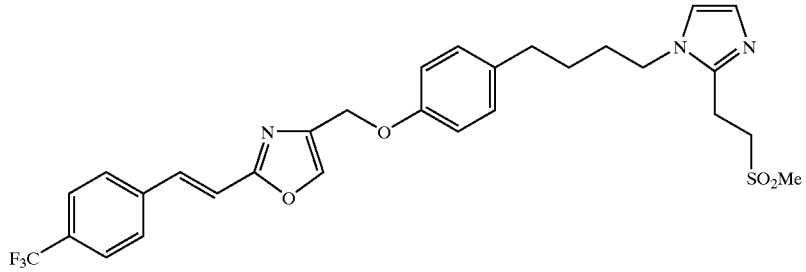

(i) Production of 4-[[4-[4-[2-[2-(methylsulfanyl)ethyl]-1H-imidazol-1-yl]butyl]phenoxy]methyl]-2-[(E)-2-[4-(trifluoromethyl)phenyl]ethenyl]-1,3-oxazole Using 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]-1-ethanol (1.00 g), triethylamine (0.544 ml), methanesulfonyl chloride (0.182 ml) and sodium thiomethoxide (288 mg), the same reaction as Reference Example 6-(iii) was carried out to yield the titled compound (761 mg) as a colorless amorphous form.

$^1$H-NMR(CDCl$_3$) δ: 1.62–1.72 (4H, m), 2.11 (3H, s), 2.59 (2H, t, J=7.0 Hz), 2.89–2.96 (4H, m), 3.86 (2H, t, J=7.4 Hz), 5.02 (2H, s), 6.80 (1H, s), 6.95–7.10 (6H, m), 7.52–7.69 (6H, m). IR (KBr): 1510, 1325, 1167, 1123, 1067 cm$^{-1}$.

(ii) Production of 4-[[4-[4-[2-[2-(methylsulfinyl)ethyl]-1H-imidazol-1-yl]butyl]phenoxy]methyl]-2-[(E)-2-[4-(trifluoromethyl)phenyl]ethenyl]-1,3-oxazole Using 4-[[4-[4-[2-[2-(methylsulfanyl)ethyl]-1H-imidazol-1-yl]butyl]phenoxy]methyl]-2-[(E)-2-[4-(trifluoromethyl)phenyl]ethenyl]-1,3-oxazole (250 mg) and 70% m-chloroperbenzoic acid (114 mg), the same reaction as Example 11-(ii) was carried out to yield the titled compound (190 mg) as a colorless amorphous form.

$^1$H-NMR(CDCl$_3$) δ: 1.56–1.80 (4H, m), 2.59 (2H, t, J=7.0 Hz), 2.61 (3H, s), 3.06–3.16 (3H, m), 3.32–3.40 (1H, m), 3.89 (2H, t, J=7.2 Hz), 5.02 (2H, d, J=1.2 Hz), 6.84 (1H, d, J=1.4 Hz), 6.90–7.10 (6H, m), 7.52–7.69 (6H, m). IR (KBr): 1510, 1325, 1167, 1121, 1067 cm$^{-1}$.

Example 16

Production of N-[2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethyl]methanesulfonamide

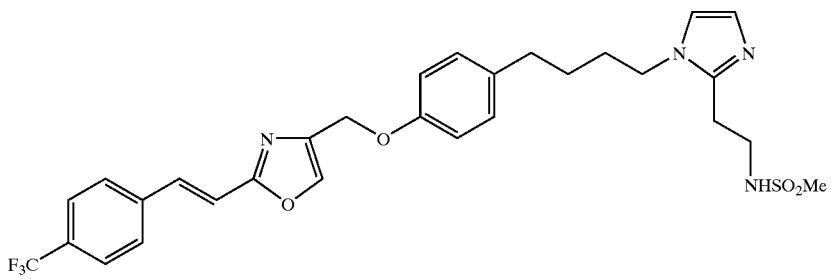

Triethylamine (109 μl) and methanesulfonyl chloride (36.4 μl) were added to a solution of 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethylamine (200 mg) in THF (4 ml) at 0° C., and the mixture was stirred at 0° C. for 1 hr. The reaction mixture was combined with water and extracted with ethyl acetate. The extract was washed with saturated brine and dried over anhydrous magnesium sulfate. The solvent was evaporated under reduced pressure, and the residue was purified by silica gel column chromatography (Chromatorex; eluent; ethyl acetate) and recrystallized from ethyl acetate-hexane to give the titled compound (126 mg) as colorless needle crystals.

$^{1}$H-NMR (CDCl$_3$) δ: 1.63–1.79 (4H, m), 2.61 (2H, t, J=6.6-Hz), 2.96 (3H, s), 3.07–3.12 (2H, m), 3.61–3.67 (2H, m), 3.90–3.96 (2H, m), 5.02 (2H, s), 6.34 (1H, br s), 6.92–7.10 (7H, m), 7.53–7.70 (6H, m). IR (KBr): 1510, 1325, 1242, 1123, 1069 cm$^{-1}$.

Example 17

Production of 4-[[4-[4-[2-[2-(methylsulfonyl)ethyl]-1H-imidazol-1-yl]butyl]phenoxy]methyl]-2-[(E)-2-[4-(trifluoromethyl)phenyl]ethenyl]-1,3-oxazole

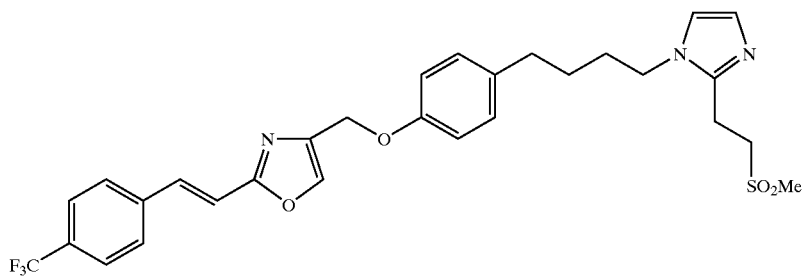

Using 4-[[4-[4-[2-[2-(methylsulfanyl)ethyl]-1H-imidazol-1-yl]butyl]phenoxy]methyl]-2-[(E)-2-[4-(trifluoromethyl)phenyl]ethenyl]-1,3-oxazole (248 mg) and 70% m-chloroperbenzoic acid (282 mg), the same reaction as Example 11-(ii) was carried out to yield the titled compound (133 mg) as colorless needle crystals.

$^{1}$H-NMR(CDCl$_3$) δ: 1.61–1.76 (4H, m), 2.60 (2H, t, J=7.4 Hz), 2.84 (3H, s), 3.15 (2H, t, J=7.2 Hz), 3.63 (2H, t, J=7.2 Hz), 3.88 (2H, t, J=7.0 Hz), 5.02 (2H, d, J=0.8 Hz), 6.84 (1H, d, J=1.6 Hz), 6.91–7.10 (6H, m), 7.52–7.69 (6H, m). IR (KBr): 1510, 1325, 1310, 1127, 1067 cm$^{-1}$.

Example 18

Production of methyl[1-(4-{4-[(2-{(E)-2-[4-(trifluoromethyl)phenyl]ethenyl}-1,3-oxazol-4-yl)methoxy]phenyl}butyl)-1H-1,2,3-triazol-4-yl] methylsulfone

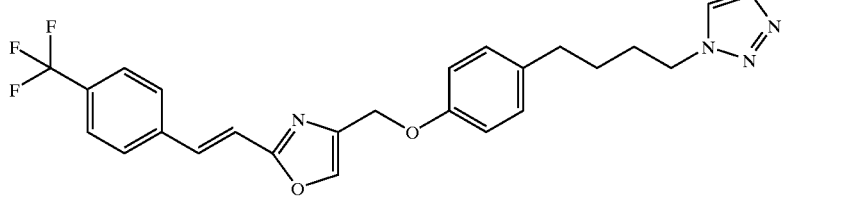

(i) Production of ethyl 1-(4-{4-[(2-{(E)-2-[4-(trifluoromethyl)phenyl]ethenyl}-1,3-oxazol-4-yl)methoxy]phenyl}butyl)-1H-1,2,3-triazole-4-carboxylate Potassium carbonate (2.4 g) was added to a solution of 4-[[4-(4-iodobutyl)phenoxy]methyl]-2-{(E)-2-[4-(trifluoromethyl)phenyl]ethenyl}-1,3-oxazole (7.5 g) and ethyl 1H-1,2,3-triazole-4-carboxylate (2.1 g) in dimethylformamide (100 ml), and the mixture was stirred at 70° C. for 5 hr. After the reaction was completed, the reaction mixture was combined with water and extracted with ethyl acetate. The extract was washed with saturated brine and dried over anhydrous magnesium sulfate. The solvent was evaporated under reduced pressure, and the residue was purified by silica gel column chromatography (eluent; ethyl acetate:hexane=3:1), and recrystallized from ethyl acetate-hexane to give the titled compound (1.85 g) as a colorless crystal powder.

$^{1}$H-NMR(CDCl$_3$) δ: 1.41 (3H, t, J=7.2 Hz ), 1.60–1.68 (2H, m), 1.90–1.98 (2H, m), 2.61 (2H, t, J=7.8 Hz), 4.42 (2H, q, J=7.2 Hz), 4.44 (2H, t, J=6.6 Hz), 5.02 (2H, d, J=0.6 Hz), 6.92 (2H, d, J=8.1 Hz), 7.02 (1H, d, J=16.2 Hz), 7.07 (2H, d, J=8.1 Hz), 7.56 (1H, d, J=16.2 Hz), 7.65 (4H, br s), 7.69 (1H, s), 8.02 (1H, s). IR (KBr): 3131, 1699, 1512, 1331, 1236 cm$^{-1}$.

(ii) Production of [1-(4-{4-[(2-{(E)-2-[4-(trifluoromethyl)phenyl]ethenyl}-1,3-oxazol-4-yl)methoxy]phenyl}butyl)-1H-1,2,3-triazol-4-yl] methanol Lithium aluminium hydride (35 mg) was added to a solution of ethyl 1-(4-{4-[(2-{(E)-2-[4-(trifluoromethyl)phenyl]ethenyl}-1,3-oxazol-4-yl)methoxy]phenyl}butyl)-1H-1,2,3-triazole-4-carboxylate (500 mg) in THF (10 ml) at 0° C., and the mixture was stirred for 30 min. After the reaction was completed, the reaction mixture was combined with diethyl ether and water and filtered with Celite. The solvent was evaporated under reduced pressure, and the residue was recrystallized from ethyl acetate-hexane to give the titled compound (435 mg) as a colorless crystal powder.

$^{1}$H-NMR(CDCl$_3$) δ: 1.60–1.68 (2H, m), 1.87–1.95 (2H, m), 2.20 (1H, br s), 2.60 (2H, t, J=9.0 Hz), 4.35 (2H, t, J=7.2 Hz), 4.80 (2H, s), 5.02 (2H, d, J=0.6 Hz), 6.92 (2H, d, J=8.7 Hz), 7.02 (1H, d, J=16.2 Hz), 7.07 (2H, d, J=8.7 Hz), 7.46 (1H, s), 7.55 (1H, d, J=16.2 Hz), 7.65 (4H, br s), 7.69 (1H, s). IR (KBr): 3204, 1615, 1514, 1323, 1127 cm$^{-1}$.

(iii) Production of 4-(4-{4-[(methylsulfanyl)methyl]-1H-1,2,3-triazol-1-yl}butyl) phenyl(2-{(E)-2-[4-(trifluoromethyl)phenyl]ethenyl}-1,3-oxazol-4-yl)methyl ether Pyridine (0.81 ml), tributylphosphine (0.75 ml) and dimethyl disulfide (0.27 ml) were added to a solution of [1-(4-{4-[(2-{(E)-2-[4-(trifluoromethyl)phenyl]ethenyl}-1,3-oxazol-4-yl)methoxy]phenyl}butyl)-1H-1,2,3-triazol-4-yl] methanol (500 mg) in dichloromethane (10 ml), and the mixture was stirred at room temperature for 5 hr. After the reaction was completed, the reaction mixture was combined with 10% aqueous hydrochloric acid solution and extracted with ethyl acetate. The extract was washed with saturated brine and dried over anhydrous magnesium sulfate. The solvent was evaporated under reduced pressure, and the residue was purified by silica gel column chromatography (eluent; ethyl acetate:hexane=2:1) and recrystallized from ethyl acetate-hexane to give the titled compound (454 mg) as a colorless crystal powder.
$^1$H-NMR(CDCl$_3$) δ: 1.59–1.68 (2H, m), 1.87–1.98 (2H, m), 2.11 (3H, s), 2.61 (2H, t, J=7.8 Hz), 3.78 (2H, s), 4.34 (2H, t, J=7.2 Hz), 5.02 (2H, s), 6.92 (2H, d, J=8.7 Hz), 7.02 (1H, d, J=16.2 Hz), 7.07 (2H, d, J=8.7 Hz), 7.43 (1H, s), 7.58 (1H, d, J=16.2 Hz), 7.60 (4H, br s), 7.69 (1H, s). IR (KBr): 3127, 1615, 1514, 1329, 1119 cm$^{-1}$.

(iv) Production of methyl[1-(4-{4-[(2-{(E)-2-[4-(trifluoromethyl)phenyl]ethenyl}-1,3-oxazol-4-yl)methoxy]phenyl}butyl)-1H-1,2,3-triazol-4-yl] methylsulfone m-Chloroperbenzoic acid (70%, 187 mg) was added to a solution of 4-(4-{4-[(methylsulfanyl)methyl]-1H-1,2,3-triazol-1-yl}butyl) phenyl(2-{(E)-2-[4-(trifluoromethyl)phenyl]ethenyl}-1,3-oxazol-4-yl)methyl ether (160 mg) in dichloromethane (5 ml) at 0° C., and the mixture was stirred for 1 hr. After the reaction was completed, the reaction mixture was combined with 10% aqueous sodium hydroxide solution and extracted with ethyl acetate. The extract was washed with saturated brine and dried over anhydrous magnesium sulfate. The solvent was evaporated under reduced pressure, and the residue was purified by silica gel column chromatography (eluent; ethyl acetate:hexane=2:1) and recrystallized from ethyl acetate to give the titled compound (131 mg) as a pale yellow crystal powder.
$^1$H-NMR(CDCl$_3$) δ: 1.61–1.69 (2H, m), 1.90–1.98 (2H, m), 2.62 (2H, t, J=7.5 Hz), 2.88 (3H, s), 4.38 (2H, t, J=6.9 Hz), 4.40 (2H, s), 5.02 (2H, s), 6.92 (2H, d, J=8.7 Hz), 7.02 (1H, d, J=16.2 Hz), 7.08 (2H, d, J=8.7 Hz), 7.56 (1H, d, J=16.2 Hz), 7.64 (4H, br s), 7.69 (2H, s). IR (KBr): 3120, 1615, 1514, 1323, 1128 cm$^{-1}$.

Example 19

Production of 2-[(E)-2-(4-fluorophenyl)ethenyl]-4-[[4-[4-[2-[(methylsulfonyl)methyl]-1H-imidazol-1-yl]butyl]phenoxy]methyl]-1,3-oxazole

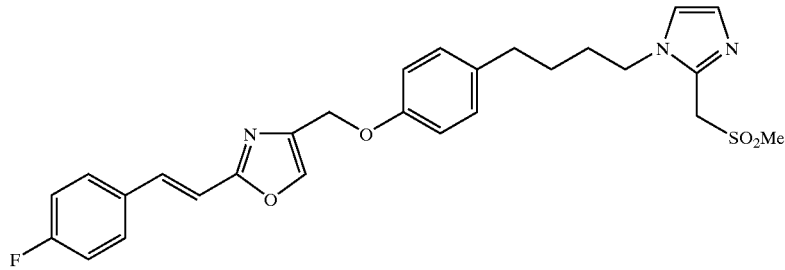

Using 2-[(E)-2-(4-fluorophenyl)ethenyl]-4-(chloromethyl)-1,3-oxazole (274 mg), 4-[4-[2-[(methylsulfonyl)methyl]-1H-imidazol-1-yl]butyl]phenol (300 mg) and 65% sodium hydride (39.5 mg), the same reaction as Example 11-(i) was carried out to yield the titled compound (275 mg) as a colorless crystal powder.
$^1$H-NMR(CDCl$_3$) δ: 1.63–1.85 (4H, m), 2.61 (2H, t, J=7.0 Hz), 2.96 (3H, s), 4.03 (2H, t, J=7.6 Hz), 4.36 (2H, s), 5.01 (2H, d, J=0.6 Hz), 6.81–7.13 (9H, m), 7.46–7.55 (3H, m), 7.66 (1H, s). IR (KBr): 1510, 1312, 1235, 1136, 826 cm$^{-1}$.

Example 20

Production of 2-[(E)-2-(2,4-difluorophenyl)ethenyl]-4-[[4-[4-[2-[(methylsulfonyl)methyl]-1H-imidazol-1-yl]butyl]phenoxy]methyl]-1,3-oxazole

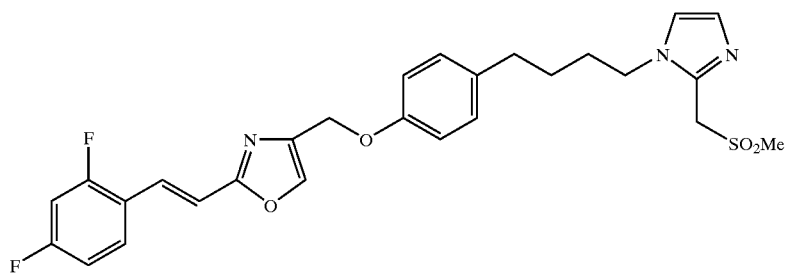

Using 4-(chloromethyl)-2-[(E)-2-(2,4-difluorophenyl)ethenyl]-1,3-oxazole (274 mg), 4-[4-[2-[(methylsulfonyl)methyl]-1H-imidazol-1-yl]butyl]phenol (300 mg) and 65% sodium hydride (39.5 mg), the same reaction as Example 11-(i) was carried out to yield the titled compound (285 mg) as a colorless crystal powder.

$^1$H-NMR(CDCl$_3$) δ: 1.64–1.80 (4H, m), 2.61 (2H, t, J=7.4 Hz), 3.00 (3H, s), 4.03 (2H, t, J=7.4 Hz), 4.36 (2H, s), 5.02 (2H, s), 6.87–7.11 (7H, m), 7.34–7.53 (4H, m), 7.66 (1H, s). IR (KBr): 1510, 1310, 1275, 1140, 966 cm$^{-1}$.

Example 21

Production of 2-[(E)-2-(4-chlorophenyl)ethenyl]-4-[[4-[4-[2-[(methylsulfonyl)methyl]-1H-imidazol-1-yl]butyl]phenoxy]methyl]-1,3-oxazole

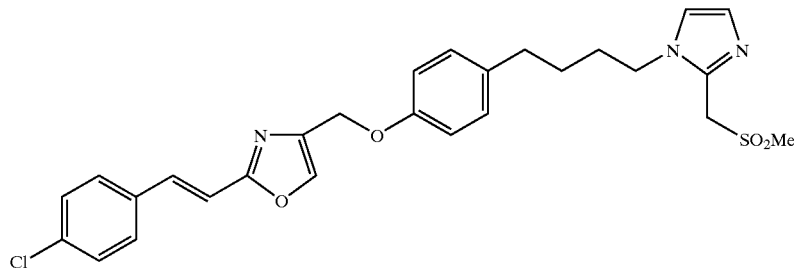

Using 4-(chloromethyl)-2-[(E)-2-(4-chlorophenyl)ethenyl]-1,3-oxazole (227 mg), 4-[4-[2-[(methylsulfonyl)methyl]-1H-imidazol-1-yl]butyl]phenol (250 mg) and 65% sodium hydride (32.9 mg), the same reaction as Example 11-(i) was carried out to yield the titled compound (322 mg) as a colorless crystal powder.

$^1$H-NMR(CDCl$_3$) δ: 1.60–1.85 (4H, m), 2.61 (2H, t, J=7.8 Hz), 2.97 (3H, s), 4.03 (2H, t, J=7.0 Hz), 4.36 (2H, s), 5.03 (2H, d, J=0.6 Hz), 6.90–7.33 (11H, m), 7.61 (1H, d, J=16.8 Hz), 7.69 (1H, s). IR (KBr): 1512, 1310, 1252, 1136, 816 cm$^{-1}$.

Example 22

Production of 2-[(E)-2-(2,6-difluorophenyl)ethenyl]-4-[[4-[4-[2-[(methylsulfonyl)methyl]-1H-imidazol-1-yl]butyl]phenoxy]methyl]-1,3-oxazole

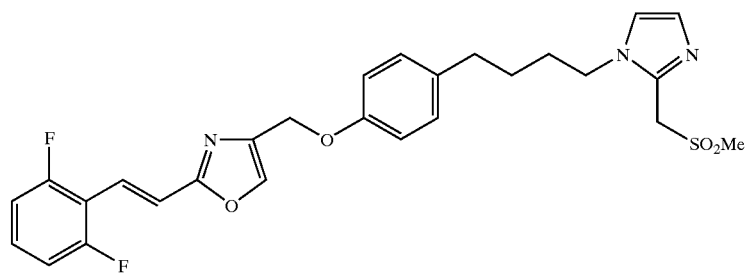

Using 4-(chloromethyl)-2-[(E)-2-(2,6-difluorophenyl)ethenyl]-1,3-oxazole (228 mg), 4-[4-[2-[(methylsulfonyl)methyl]-1H-imidazol-1-yl]butyl]phenol (250 mg). and 65% sodium hydride (32.9 mg), the same reaction as Example 11-(i) was carried out to yield the titled compound (280 mg) as colorless needle crystals.

$^1$H-NMR(CDCl$_3$) δ: 1.60–1.85 (4H, m), 2.61 (2H, t, J=7.4 Hz), 2.97 (3H, s), 4.03 (2H, t, J=7.0 Hz), 4.36 (2H, s), 5.02 (2H, d, J=0.8 Hz), 6.81–7.11 (9H, m), 7.48–7.67 (3H, m). IR (KBr): 1510, 1310, 1240, 1136, 1001 cm$^{-1}$.

Example 23

Production of 2-[(E)-2-(4-bromophenyl)ethenyl]-4-[[4-[4-[2-[(methylsulfonyl)methyl]-1H-imidazol-1-yl]butyl]phenoxy]methyl]-1,3-oxazole

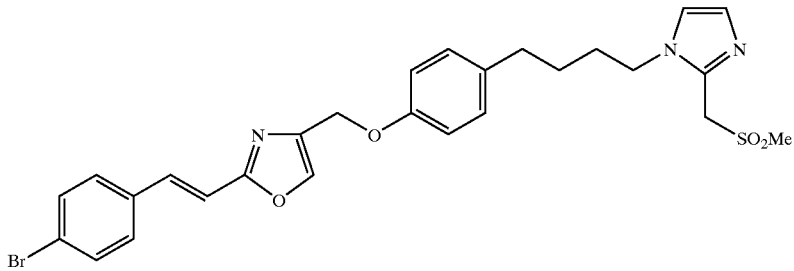

Using 2-[(E)-2-(4-bromophenyl)ethenyl]-4-(chloromethyl)-1,3-oxazole (266 mg), 4-[4-[2-[(methylsulfonyl)methyl]-1H-imidazol-1-yl]butyl]phenol (250 mg) and 65% sodium hydride (32.9 mg), the same reaction as Example 11-(i) was carried out to yield the titled compound (361 mg) as a colorless crystal powder.

$^1$H-NMR(CDCl$_3$) δ: 1.59–1.85 (4H, m), 2.61 (2H, t, J=7.2 Hz), 2.96 (3H, s), 4.03 (2H, t, J=7.0 Hz), 4.36 (2H, s), 5.02 (2H, s), 6.88–7.11 (7H, m), 7.36–7.54 (5H, m), 7.66 (1H, s). IR (KBr): 1512, 1308, 1254, 1138, 814 cm$^{-1}$.

Example 24

Production of 2-[(E)-2-(4-chloro-2-fluorophenyl)ethenyl]-4-[[4-[4-[2-[(methylsulfonyl)methyl]-1H-imidazol-1-yl]butyl]phenoxy]methyl]-1,3-oxazole

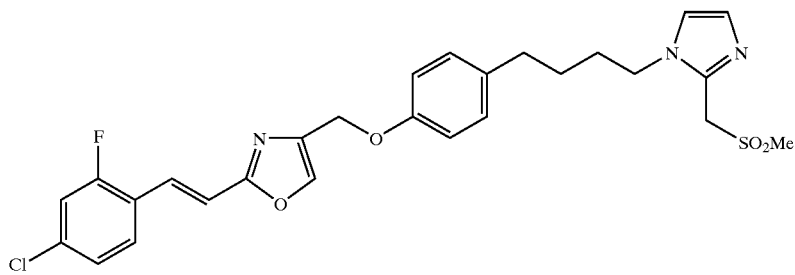

Using 2-[(E)-2-(4-chloro-2-fluorophenyl)ethenyl]-4-(chloromethyl)-1,3-oxazole (243 mg), 4-[4-[2-[(methylsulfonyl)methyl]-1H-imidazol-1-yl]butyl]phenol (250 mg) and 65% sodium hydride (35.9 mg), the same reaction as Example 11-(i) was carried out to yield the titled compound (105 mg) as a colorless crystal powder.

$^1$H-NMR(CDCl$_3$) δ: 1.62–1.69 (2H, m), 1.75–1.85 (2H, m), 2.61 (2H, t, J=7.5 Hz), 2.97 (3H, s), 4.03 (2H, t, J=7.5 Hz), 4.36 (2H, s), 5.02 (2H, d, J=0.6 Hz), 6.91–7.19 (9H, m), 7.49 (1H, d, J=8.1, 8.1 Hz), 7.59 (1H, d, J=16.5 Hz), 7.68 (1H, s). IR (KBr): 1510, 1485, 1306, 1246, 1136 cm$^{-1}$.

Example 25

Production of 2-[(E)-2-(2,4-dichlorophenyl)ethenyl]-4-[[4-[4-[2-[(methylsulfonyl)methyl]-1H-imidazol-1-yl]butyl]phenoxy]methyl]-1,3-oxazole

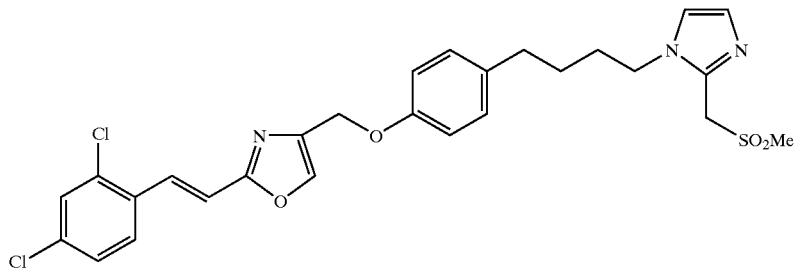

Using 4-(chloromethyl)-2-[(E)-2-(2,4-dichlorophenyl)ethenyl]-1,3-oxazole (257 mg), 4-[4-[2-[(methylsulfonyl)methyl]-1H-imidazol-1-yl]butyl]phenol (250 mg) and 65% sodium hydride (35.9 mg), the same reaction as Example 11-(i) was carried out to yield the titled compound (246 mg) as a-colorless crystal powder.

$^1$H-NMR(CDCl$_3$) δ: 1.61–1.69 (2H, m), 1.75–1.83 (2H, m), 2.61 (2H, t, J=7.5 Hz), 2.97 (3H, s), 4.03 (2H, t, J=7.5 Hz), 4.36 (2H, s), 5.03 (2H, d, J=0.9 Hz), 6.90–6.96 (4H, m), 7.05–7.10 (3H, m), 7.27–7.30 (1H, m), 7.45 (1H, d, J=2.1 Hz), 7.59 (1H, d, J=4.2 Hz), 7.69 (1H, s), 7.84 (1H, d, J=16.5 Hz). IR (KBr): 1510, 1310, 1244, 1136, 1101 cm$^{-1}$.

Example 26

2-[(E)-2-(4-bromo-2-fluorophenyl)ethenyl]-4-[[4-[2-[(methylsulfonyl)methyl]-1H-imidazol-1-yl]butyl]phenoxy]methyl]-1,3-oxazole

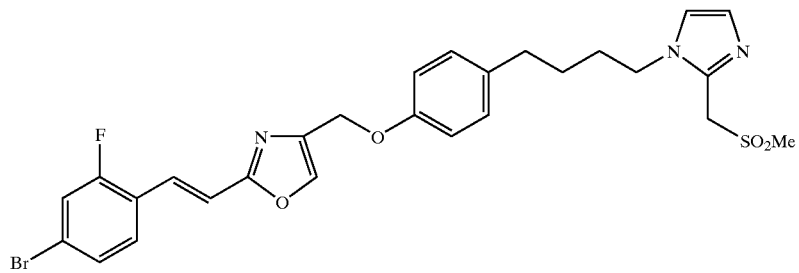

Using 2-[(E)-2-(4-bromo-2-fluorophenyl)ethenyl]-4-(chloromethyl)-1,3-oxazole (282 mg), 4-[4-[2-[(methylsulfonyl)methyl]-1H-imidazol-1-yl]butyl]phenol (250 mg) and 65% sodium hydride (32.9 mg), the same reaction as Example 11-(i) was carried out to yield the titled compound (313 mg) as a colorless crystal powder.

$^1$H-NMR(CDCl$_3$) δ: 1.60–1.80 (4H, m), 2.61 (2H, t, J=7.2 Hz), 2.96 (3H, s), 4.03 (2H, t, J=7.6 Hz), 4.36 (2H, s), 5.02 (2H, d, J=0.6 Hz), 6.90–7.11 (7H, m), 7.28–7.47 (3H, m), 7.57 (1H, d, J=16.4 Hz), 7.68 (1H, s). IR (KBr): 1514, 1310, 1248, 1175, 1130 cm$^{-1}$.

Example 27

Production of 2-[(E)-2-(3,4-difluorophenyl)ethenyl]-4-[[4-[4-[2-[(methylsulfonyl)methyl]-1H-imidazol-1-yl]butyl]phenoxy]methyl]-1,3-oxazole

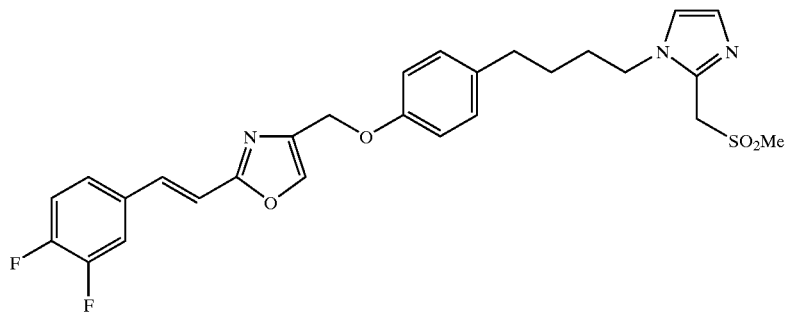

Using 4-(chloromethyl)-2-[(E)-2-(3,4-difluorophenyl)ethenyl]-1,3-oxazole (228 mg), 4-[4-[2-[(methylsulfonyl)methyl]-1H-imidazol-1-yl]butyl]phenol (250 mg) and 65% sodium hydride (32.9 mg), the same reaction as Example 11-(i) was carried out to yield the titled compound (261 mg) as colorless flaky crystals.

$^1$H-NMR(CDCl$_3$) δ: 1.59–1.80 (4H, m), 2.61 (2H, t, J=7.6 Hz), 2.96 (3H, s), 4.03 (2H, t, J=7.4 Hz), 4.36 (2H, s), 5.01 (2H, s), 6.80–6.96 (4H, m), 7.04–7.48 (7H, m), 7.67 (1H, s). IR (KBr): 1512, 1300, 1275, 1246, 1136 cm$^{-1}$.

Example 28

Production of 2-[(E)-2-(2-chloro-4-fluorophenyl)ethenyl]-4-[[4-[4-[2-[(methylsulfonyl)methyl]-1H-imidazol-1-yl]butyl]phenoxy]methyl]-1,3-oxazole

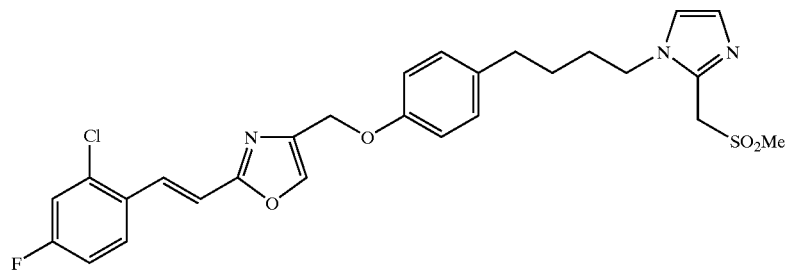

Using 2-[(E)-2-(2-chloro-4-fluorophenyl)ethenyl]-4-(chloromethyl)-1,3-oxazole (243 mg), 4-[4-[2-[(methylsulfonyl)methyl]-1H-imidazol-1-yl]butyl]phenol (250 mg) and 65% sodium hydride (32.9 mg), the same reaction as Example 11-(i) was carried out to yield the titled compound (304 mg) as colorless needle crystals.

$^1$H-NMR(CDCl$_3$) δ: 1.62–1.81 (4H, m), 2.61 (2H, t, J=7.2 Hz), 2.97 (3H, s), 4.03 (2H, t, J=7.0 Hz), 4.36 (2H, s), 5.02 (2H, d, J=0.8 Hz), 6.84–7.11 (8H, m), 7.18 (1H, dd, J=2.6, 8.4 Hz), 7.00–7.68 (2H, m), 7.85 (1H, d, J=16.0 Hz). IR (KBr): 1510, 1485, 1310, 1246, 1136 cm$^{-1}$.

Example 29

Production of 2-[(E)-2-(4-chloro-3-fluorophenyl)ethenyl]-4-[[4-[4-[2-[(methylsulfonyl)methyl]-1H-imidazol-1-yl]butyl]phenoxy]methyl]-1,3-oxazole

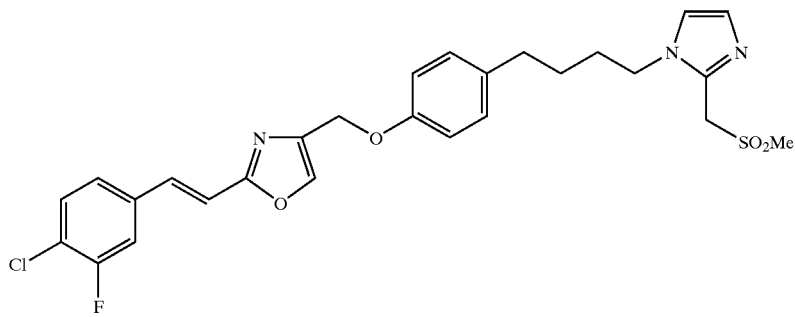

Using 2-[(E)-2-(4-chloro-3-fluorophenyl)ethenyl]-4-(chloromethyl)-1,3-oxazole (291 mg), 4-[4-[2-[(methylsulfonyl)methyl]-1H-imidazol-1-yl]butyl]phenol (300 mg) and 65% sodium hydride (39.5 mg), the same reaction as Example 11-(i) was carried out to yield the titled compound (333 mg) as colorless needle crystals.

$^1$H-NMR (CDCl$_3$) δ: 1.64–1.80 (4H, m), 2.61 (2H, t, J=6.6 Hz), 2.96 (3H, s), 4.03 (2H, t, J=7.0 Hz), 4.36 (2H, s), 5.02 (2H, d, J=0.8 Hz), 6.86–6.95 (3H, m), 7.04–7.11 (2H, m), 7.22–7.49 (6H, m), 7.67 (1H, s). IR (KBr): 1512, 1306, 1244, 1132, 968 cm$^{-1}$.

Example 30

Production of 2-[(E)-2-[4-(trifluoromethyl)phenyl] ethenyl]-4-[[4-[4-[2-[[(trifluoromethyl)sulfonyl] methyl]-1H-imidazol-1-yl]butyl]phenoxy]methyl]-1,3-oxazole

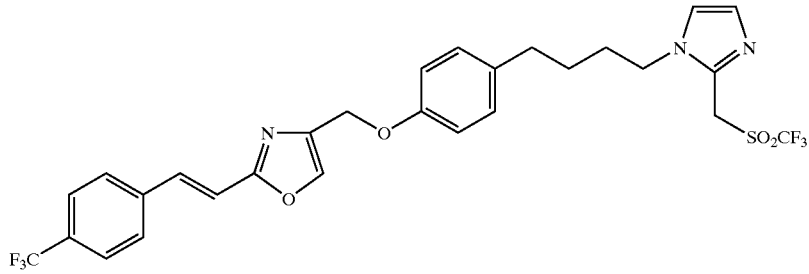

Triethylamine (91.0 μl), trimethyl phosphite (77.0 μl) and trifluoromethanesulfonyl chloride (69.5 μl) were added to a solution of [1-[4-[4-[[2-[(E)-2-[4-(trifluoromethyl)phenyl] ethenyl]-1,3-oxazol-4-yl]methoxy]phenyl]butyl]-1H-imidazol-2-yl]methanol (250 mg, 0.503 mmol) in THF (5 ml) at −30° C., and the mixture was stirred at the same temperature for 20 min and at room temperature for 1 hr. The reaction mixture was combined with water and extracted with ethyl acetate. The extract was washed with saturated brine and dried over anhydrous magnesium sulfate. The solvent was evaporated under reduced pressure, and the residue was purified by silica gel column chromatography (eluent; hexane:ethyl acetate=1:1) and recrystallized from ethyl acetate-hexane to give the titled compound (38 mg) as a colorless crystal powder.

$^1$H-NMR (CDCl$_3$) δ: 1.59–1.87 (4H, m), 2.61 (2H, t, J=7.4 Hz), 4.01 (2H, t, J=7.0 Hz), 4.68 (2H, s), 5.02 (2H, s), 6.91–7.11 (7H, m), 7.52–7.69 (6H, m). IR (KBr): 1368, 1325, 1202, 1132, 1121 cm$^{-1}$.

Example 31

Production of 2,2,2-trifluoro-N-[2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethyl] ethanesulfonamide

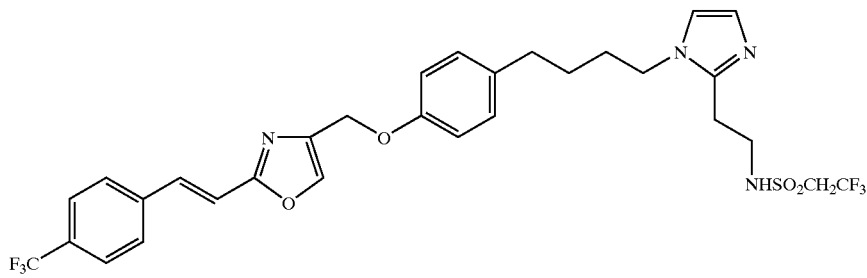

Triethylamine (137 μl) and 2,2,2-trifluoroethanesulfonyl chloride (65.0 l) were added to a solution of 2-[1-[4-[4-[[2-[(E)-2-[4-(trifluoromethyl)phenyl]ethenyl]-1,3-oxazol-4-yl] methoxy]phenyl]butyl]-1H-imidazol-2-yl]ethylamine (250 mg) in THF (5 ml) at 0° C., and the mixture was stirred at the same temperature for 110 min. The reaction mixture was combined with water and extracted with ethyl acetate. The extract was washed with water and dried over anhydrous magnesium sulfate. The solvent was evaporated under reduced pressure, and the residue was purified by silica gel column chromatography (Chromatorex) (eluent; hexane-:ethyl acetate=1:2 to 1:4) and recrystallized from ethyl acetate-methanol-hexane to give the titled compound (48 mg) as colorless needle crystals.

$^1$H-NMR (CDCl$_3$) δ: 1.60–1.73 (4H, m), 2.59 (2H, t, J=7.2 Hz), 2.82 (2H, t, J=6.0 Hz), 3.63 (2H, t, J=6.0 Hz), 3.75–3.89 (4H, m), 5.02 (2H, d, J=1.2 Hz), 6.82 (1H, d, J=1.6 Hz), 6.90–7.10 (6H, m), 7.52–7.69 (6H, m). IR (KBr): 1346, 1325, 1155, 1127, 1071 cm$^{-1}$.

Example 32

Production of N-[2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethyl]-2-propanesulfonamide

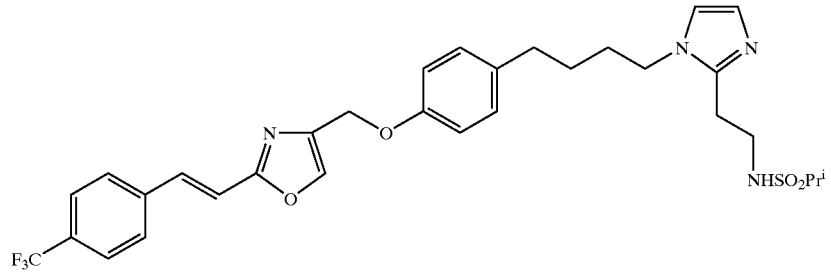

Using 2-[1-[4-[4-[[2-[(E)-2-[4-(trifluoromethyl)phenyl]ethenyl]-1,3-oxazol-4-yl]methoxy]phenyl]butyl]-1H-imidazol-2-yl]ethylamine (248 mg), triethylamine (135 µl) and 2-propanesulfonyl chloride (65.5 µl), the same reaction as Example 31 was carried out to yield the titled compound (55 mg) as colorless needle crystals.

$^1$H-NMR(CDCl$_3$) δ: 1.39 (6H, d, J=6.6 Hz), 1.64–1.81 (4H, m), 2.59 (2H, t, J=7.4 Hz), 2.84 (2H, t, J=5.6 Hz), 3.14–3.25 (1H, m), 3.55–3.64 (2H, m), 3.81 (2H, t, J=6.6 Hz), 5.02 (2H, s), 5.85 (1H, br s), 6.81(1H, d, J=1.4 Hz), 6.90–7.10 (6H, m), 7.52–7.69 (6H, m). IR (KBr): 1510, 1325, 1167, 1125, 1067 cm$^{-1}$.

Example 33

Production of 4-[2-(4-{4-[2-(methylsulfonyl)methyl-1H-imidazol-1-yl]butyl}phenoxy)ethyl]-2-{(E)-2-[4-(trifluoromethyl)phenyl]ethenyl}-1,3-oxazole

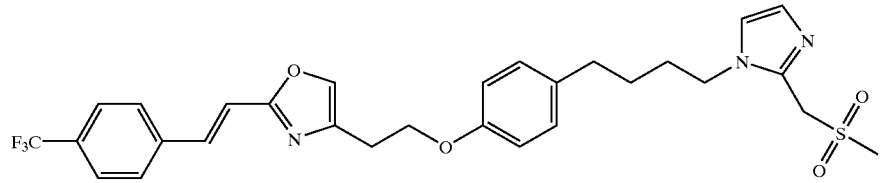

(i) Production of ethyl (E)-2-(4-trifluoromethyl)phenyl)ethenyl]-1,3-oxazol-4-yl]acetate A solution of (E)-2-(4-trifluoromethylphenyl)ethenylamide (10.0 g) and ethyl 4-chloroacetoacetate (13.5 g) in toluene (60 ml) was refluxed for 16 hr by use of Dean-Stark apparatus. The reaction mixture was combined with water and extracted with ethyl acetate. The extract was dried over anhydrous magnesium sulfate. The solvent was evaporated under reduced pressure, and the residue was purified by silica gel column chromatography (eluent; ethyl acetate:hexane=1:2) and recrystallized from ethyl acetate-hexane to give the titled compound (8.34 g) as a colorless crystal powder.

$^1$H-NMR(CDCl$_3$) δ: 1.30 (3H, t, J=7.0 Hz), 3.65 (2H, s), 4.22 (2H, q, J=7.0 Hz), 6.99 (1H, d, J=16.4 Hz), 7.51 (1H, d, J=16.4 Hz), 7.63 (4H, s), 7.66 (1H, s). IR (KBr): 2988, 1741, 1329, 1246, 1155, 1120 cm$^{-1}$.

(ii) Production of 2-[[(E)-2-(4-(trifluoromethyl)phenyl)ethenyl]-1,3-oxazol-4-yl]ethanol Ethyl [[(E)-2-(4-(trifluoromethyl)phenyl)ethenyl]-1,3-oxazol-4-yl]acetate (1.72 g) was added to a suspension of calcium chloride (2.35 g) and sodium borohydride (1.60 g) in THF-ethanol (10 ml- 10 ml) at 0° C., and the mixture was stirred for 1 hr. The reaction mixture was combined with 1N hydrochloric acid and extracted with ethyl acetate. The extract was washed with saturated brine and dried over anhydrous magnesium sulfate. The solvent was evaporated, and the residue was purified by silica gel column chromatography (eluent; ethyl acetate:hexane=1:1 to ethyl acetate) to give the titled compound (1.27 g) as a colorless crystal powder.

$^1$H-NMR(CDCl$_3$) δ: 2.67 (1H, br s), 2.84 (2H, t, J=5.8 Hz), 3.96 (2H, m), 7.00 (1H, d, J=16.6 Hz), 7.49–7.66 (6H, m). IR (KBr): 3314, 1593, 1415, 1325, 1180, 1107 cm$^{-1}$.

(iii) Production of 4-[2-(4-{4-[2-(methylsulfonyl)methyl-1H-imidazol-1-yl]butyl}phenoxy)ethyl]-2-{(E)-2-[4-(trifluoromethyl)phenyl]ethenyl}-1,3-oxazole 2-{(E)-2-[4-(Trifluoromethyl)phenyl]ethenyl}-1,3-oxazol-4-yl]ethanol. (91 mg) and DEAD (40% toluene solution, 110 µl) were added to a solution of 4-{4-[2-(methylsulfonyl)methyl-1H-imidazol-1-yl]butyl}phenol (91 mg) and triphenylphosphine (78 mg) in toluene (5 ml) at −78° C., and the mixture was stirred at room temperature for 16 hr. The reaction mixture was combined with 3N aqueous sodium hydroxide solution and extracted with ethyl acetate. The extract was dried over anhydrous sodium sulfate. The solvent was evaporated under reduced pressure, and the residue was purified by silica gel column chromatography (eluent; ethyl acetate to methanol:ethyl acetate 1:100) and recrystallized from methanol-ethyl acetate-hexane to give the titled compound (39 mg) as a colorless crystal powder.

$^1$H-NMR(CDCl$_3$) δ: 1.57–1.67 (2H, m), 1.74–1.84 (2H, m), 2.59 (2H, t, J=7.2 Hz), 2.96 (3H, s), 3.05 (2H, t, J=6.3 Hz), 4.02 (2H, t, J=7.2 Hz), 4.24 (2H, t, J=6.3 Hz), 4.35 (2H, s), 6.85–7.08 (7H, m), 7.50 (1H, d, J=18.0 Hz), 7.53 (1H, s), 7.63 (4H, s). IR (KBr): 2928, 1512, 1323, 1167, 1128, 1068, 825 cm$^{-1}$.

Preparation Example 1

Amount Per Tablet

| | |
|---|---|
| (1) Compound obtained in Example 4 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 4, 60.0 mg of lactose and 35.0 mg of corn starch was granulated through a 1 mm-mesh sieve using 0.03 ml of a 10% by weight aqueous solution of gelatin (3.0 mg of gelatin), after which the granules were dried at 40° C. and filtered again. The granules obtained were mixed with 2.0 mg of magnesium stearate and compressed. The core tablets obtained were coated with a sugar coat comprising a suspension of sucrose, titanium dioxide, talc, and gum arabic and polished with beeswax to yield sugar-coated tablets.

Preparation Example 2

Dose Per Tablet

| | |
|---|---|
| (1) Compound obtained in Example 4 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 4 and 3.0 mg of magnesium stearate were granulated using 0.07 ml of an aqueous solution of soluble starch (7.0 mg of soluble starch), after which these granules were dried and mixed with 70.0 mg of lactose and 50.0 mg of corn starch. This mixture was compressed to yield tablets.

Reference Preparation Example 1

Dose Per Tablet

| | |
|---|---|
| (1) Leuproreline acetate | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of leuproreline acetate and 3.0 mg of magnesium stearate were granulated using 0.07 ml of an aqueous solution of soluble starch (7.0 mg of soluble starch), after which these granules were dried and mixed with 70.0 mg of lactose and 50.0 mg of corn starch. This mixture was compressed to yield tablets.

Preparation Example 3

The preparation obtained in Preparation Example 1 or 2 and the preparation obtained in Reference Preparation Example 1 are combined.

In the following Test Examples, Compound Numbers indicate corresponding Example Numbers (e.g., the compound of Example 2 is indicated by Compound 2).

Test Example 1

Suppression of Receptor Tyrosine-Phosphorylation in Human Breast Cancer Cells A suspension of human breast cancer cell BT-474 (500 µl (300,000 cells)) were sown into a 24-well plate, and cultured at 37° C. in the presence of 5% carbon dioxide. On the following day, 250 µl of a solution of the test compound, which was previously 4-fold diluted, was added. After 2 hours, the extraction was added to stop the reaction and the protein was extracted. This protein was subjected to protein electrophoresis to separate and transferred to a nylon filter. This filter was reacted with an anti-phosphotyrosine antibody; the reaction product was luminated. The amount of film photosensitization was determined using an image analyzer. Taking as 100% the amount of phosphorylation of the HER2 tyrosine in control group, the ratio of the amount of phosphorylation of the HER2 tyrosine in each group receiving a solution of the test compound at each concentration was determined, and the test compound concentration required to achieve 50% suppression by the test compound of the amount of phosphorylation of HER2 tyrosine ($IC_{50}$ value) was calculated.

The results are shown in Table 1.

This finding showed that the compound of the present invention potently inhibits the phosphorylation reaction of the tyrosine residue of the receptor protein of human breast cancer cells caused by activation of the receptor tyrosine kinase.

TABLE 1

| Example number (compound number) | Inhibition of intracellular HER2 phosphorylation BT-474 ($IC_{50}$: µM) |
|---|---|
| 1 | <4 |
| 3 | <4 |
| 5 | <4 |
| 6 | <4 |
| 11 | <4 |
| 16 | <4 |
| 17 | <4 |

Test Example 2

Inhibitory Action on Breast Cancer Cell BT-474 Proliferation in Vitro

A suspension of human breast cancer cell BT-474 (100 µl (6,000 cells)) were sown to a 96-well microplate and cultured at 37° C. in the presence of 5% carbon dioxide. On the following day, 100 µl of a solution of each test compound, which was previously diluted 2-fold, was added, and the cells were cultured for 5 days. After the culture medium containing the test compound was removed, the cells were washed and fixed with 50% trichloroacetic acid, after which a 0.4% (w/v) SRB solution (dissolved in 1% acetic acid) was added to stain the cells (Skehan et al., Journal of the National Cancer Institute, Vol. 82, pp. 1107–1112, 1990). After the pigment solution was removed and the plate was washed with a 1% acetic acid solution, 100 µl of an extract (10 mM Tris solution) was added to dissolve the pigment; absorbance was measured at an absorption wavelength of 550 nm to quantify the amount of cells as protein content. Taking as 100% the absorbance for the control group, which received no test compound solution, the ratio of the absorbance for each treatment group was determined, and the compound concentration required to achieve 50% suppression of the residual cell content relative to the control ($IC_{50}$ value) was calculated.

The results are shown in Table 2.

The compound of the present invention was thus shown to potently suppress the proliferation of cells of the human breast cancer cell line BT-474.

TABLE 2

| Example number (compound number) | Cell growth inhibition BT-474 ($IC_{50}$: μM) |
| --- | --- |
| 1 | <0.05 |
| 3 | <0.05 |
| 5 | <0.05 |
| 6 | <0.05 |
| 16 | 0.15 |

INDUSTRIAL APPLICABILITY

Since compound (I) of the present invention or a salt thereof possesses tyrosine kinase-inhibiting activity and is of low toxicity, it can be used to prevent or treat tyrosine kinase-dependent diseases in mammals. Tyrosine kinase-dependent diseases include diseases characterized by increased cell proliferation due to abnormal tyrosine kinase enzyme activity. Furthermore, compound (I) of the present invention or a salt thereof or a prodrug thereof specifically inhibits tyrosine kinase and is therefore also useful as a therapeutic agent for suppressing the growth of HER2-expressing cancer, or a preventive agent for preventing the transition of hormone-dependent cancer to hormone-independent cancer.

What is claimed is:

1. A compound represented by the formula:

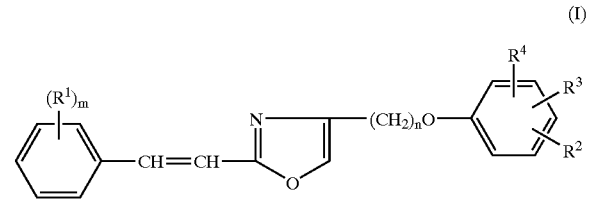

(I)

wherein m is an integer of 1 to 3; n is an integer of 1 or 2; $R^1$ is a halogen atom or an optionally halogenated $C_{1-2}$ alkyl group; each of $R^2$ and $R^3$ is, same or different, a hydrogen atom, a halogen atom, a lower alkyl group or a lower alkoxy group; $R^4$ is a group represented by the formula:

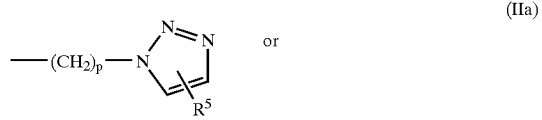

(IIa)

or

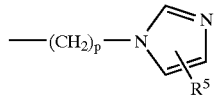

(IIb)

wherein p is an integer of 2 to 5; $R^5$ is a $C_{1-4}$ alkyl group substituted by optionally substituted alkoxycarbonyl group, optionally substituted carbamoyl group, optionally substituted cyclic aminocarbonyl group, optionally substituted carbamoyloxy group, optionally substituted cyclic aminocarbonyloxy group, optionally substituted alkylsulfonyl group, optionally substituted alkylsulfinyl group, optionally substituted sulfamoyl group, optionally substituted cyclic aminosulfonyl group, optionally substituted carbamoylamino group, optionally substituted cyclic aminocarbonylamino group, optionally substituted alkylsulfonylamino group or acylamino group; a prodrug thereof or a salt thereof.

2. The compound as defined in claim 1, wherein $R^1$ is a halogen atom or trifluoromethyl group, or a salt thereof.

3. The compound as defined in claim 1, wherein $R^5$ is methylsulfonylethyl group or methylsulfonylmethyl group, or a salt thereof.

4. The compound as defined in claim 1, wherein both of $R^2$ and $R^3$ are hydrogen atoms, or a salt thereof.

5. The compound as defined in claim 1, wherein one of $R^2$ and $R^3$ is a hydrogen atom, and the other is methyl group or methoxy group, or a sale thereof.

6. The compound as defined in claim 1, wherein the compound is N,N-dimethyl-3-[1-(4-{4-[(2-{(E)-2-[4-(trifluoromethyl)phenyl]ethenyl}-1,3-oxazol-4-yl)methoxy]phenyl}butyl)-1H-imidazol-2-yl]propanamide, N-methyl-3-[1-(4-{4-[(2-{(E)-2-[4-(trifluoromethyl)phenyl]ethenyl}-1, 3-oxazol-4-yl)methoxy]phenyl}butyl)-1H-imidazol-2-yl] propanamide, 2-[(E)-2-(2,4-difluorophenyl)ethenyl]-4-{[4-(4-{2-[2-(methylsulfonyl)ethyl]-1H-imidazol-1-yl}butyl) phenoxy]methyl}-1,3-oxazole, 4-{[4-(4-}2-[(methylsulfonyl)methyl]-1H-imidazol-1-yl}butyl) phenoxy]methyl}-2-{(E)-2-[4-(trifluoromethyl)phenyl] ethenyl}-1,3-oxazole or 4-{[4-(4-{2-[2-(methylsulfonyl) ethyl]-1H-imidazol-1-yl}butyl)phenoxy]methyl}-2-{(E)-2-[4-(trifluoromethyl)phenyl]ethenyl}-1,3-oxazole, or a salt thereof.

7. A pharmaceutical composition, which comprises the compound as defined in claim 1, or a salt thereof or a prodrug thereof, and a pharmaceutically acceptable carrier, excipient or diluent.

8. The pharmaceutical composition as described in claim 7, which is a HER2 tyrosine kinase inhibitor.

9. The pharmaceutical composition as described in claim 7, which is for treating cancer selected from the group consisting of breast cancer, prostate cancer, lung cancer and pancreatic cancer.

10. A method for treating cancer selected from the group consisting of breast cancer, prostate cancer, lung cancer and pancreatic cancer, which comprises administering an effective amount of the compound as defined in claim 1 or a salt thereof or a pro-drug thereof to a mammal in need thereof.

* * * * *